United States Patent
Fujita et al.

(10) Patent No.: US 6,720,421 B2
(45) Date of Patent: Apr. 13, 2004

(54) PHENYLURETHANE COMPOUNDS AND METHODS FOR PRODUCING SAME, ASYMMETRIC UREA COMPOUNDS AND METHODS FOR PRODUCING SAME, BARBITURIC ACID DERIVATIVE, AND DIAZO THERMAL RECORDING MATERIAL CONTAINING THE DERIVATIVE

(75) Inventors: Akinori Fujita, Shizuoka-ken (JP); Naoto Yanagihara, Shizuoka-ken (JP); Yohsuke Takeuchi, Shizuoka-ken (JP); Daisuke Arioka, Shizuoka-ken (JP); Kimi Ikeda, Shizuoka-ken (JP); Sachiko Arai, Shizuoka-ken (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 20 days.

(21) Appl. No.: 10/076,445

(22) Filed: Feb. 19, 2002

(65) Prior Publication Data

US 2002/0161225 A1 Oct. 31, 2002

(30) Foreign Application Priority Data

| Feb. 20, 2001 | (JP) | ........................................ | 2001-043649 |
| Mar. 16, 2001 | (JP) | ........................................ | 2001-077063 |
| Mar. 16, 2001 | (JP) | ........................................ | 2001-077100 |

(51) Int. Cl.[7] ............................................. C07D 234/02
(52) U.S. Cl. ...................... 544/299; 544/301; 544/302; 544/303
(58) Field of Search ................................ 544/299, 301, 544/302, 303

(56) References Cited

U.S. PATENT DOCUMENTS

| 3,477,849 A | * | 11/1969 | Becker ........................... 96/29 |
| 3,980,651 A | * | 9/1976 | Brack ........................ 260/256.4 |
| 4,283,444 A | * | 8/1981 | de Sousa et al. ............. 427/421 |
| 4,971,889 A | * | 11/1990 | Ikeda et al. ................... 430/264 |

FOREIGN PATENT DOCUMENTS

| CA | 2215585 | | 3/1998 |
| DE | 3340773 | * | 5/1985 |
| JP | 03075632 | * | 3/1991 |
| JP | 4-59288 | | 2/1992 |
| JP | 4-197782 | | 7/1992 |
| JP | 07219181 | * | 8/1995 |
| JP | 11129616 | * | 5/1999 |
| WO | WO 98/00393 | | 1/1998 |

OTHER PUBLICATIONS

Goldhahn, Die Pharmazie, vol. 12, pp. 549–555 (1957).*
Yogo et al, Journal of Heterocyclic Chemistry. vol. 18(6), pp. 1095–1100 (1981).*
Kotani et al, Journal of Medicinal Chemistry, vol. 40(5), pp. 684–694 (1997).*
Goldhahn et al, "Barbituric Acids" Pharmazie, vol. 12, pp. 549–555 (1957).*
Gordon L. Bundy et al, "Potent Renin Inhibitory Peptides Containing Hydrophilic End Groups" *Journal of Medical Chemistry*, No. 33 (1990), pp. 2276–2283.
V.V. Kuz'menko et al., "Purines and Pyrimidines and Condensed Systems Based on Them" *Chemistry of Heterocyclic Compounds*, 1987, pp. 690–697.

* cited by examiner

Primary Examiner—Mukund J. Shah
Assistant Examiner—Zachary C. Tucker
(74) Attorney, Agent, or Firm—Sughrue Mion, PLLC

(57) ABSTRACT

Phenylurethane compounds of the following general formula (1); asymmetric urea compounds of the following general formula (10) obtained from the phenylurethane compounds; barbituric acid derivatives of general formula (18) produced from the asymmetric urea compounds, which have specific substituents and are useful in diazo thermal recording materials; and diazo thermal recording materials containing the barbituric acid derivative.

General formula (1)

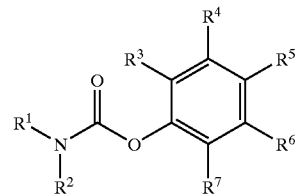

General formula (10)

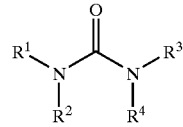

General formula (18)

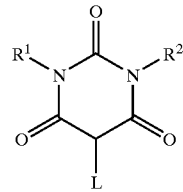

3 Claims, No Drawings

PHENYLURETHANE COMPOUNDS AND METHODS FOR PRODUCING SAME, ASYMMETRIC UREA COMPOUNDS AND METHODS FOR PRODUCING SAME, BARBITURIC ACID DERIVATIVE, AND DIAZO THERMAL RECORDING MATERIAL CONTAINING THE DERIVATIVE

BACKGROUND OF THE INVENTION

1. Field of the Invention

The present invention relates to novel phenylurethane compounds and methods for producing them, novel asymmetric urea compounds and methods for producing them, barbituric acid derivatives, and diazo thermal recording materials containing the derivatives. Precisely, the present invention relates to novel phenylurethane compounds and methods for producing them; to novel asymmetric urea compounds produced from the phenylurethane compounds and methods for producing them; as well as to barbituric acid derivatives produced from the asymmetric urea compounds and useful in diazo thermal recording materials, and to a diazo thermal recording material containing the barbituric acid derivative and having good raw-stock storability before recording thereon and good image storability after recording thereon.

2. Description of the Related Art

Heretofore, urethane compounds have had many applications in various fields of, for example, synthetic materials and medicines. Concretely, those of high molecular weight are used, for example, for urethane rubber, pastes and insulating materials; and those of low molecular weight are, for example, for reagents in alcohol identification. Further, urethane compounds are used for reactants in protecting amino compounds, and for intermediates to be reacted with other amino compounds in urea-forming reactions.

For producing urethane compounds, for example, known are a method of reacting an isocyanate with an alcohol, and a method of condensing carbamoyl chloride with an alcohol. Concretely, they include phenylurethane compounds of which the polypeptide terminal is urethanated (*J. Med. Chem.*, 33 (8), 2267–2283, 1990); phenylurethane compounds having a carboxyl group in the molecule (PCT. Int. Appl. 9800393, Jan. 8, 1998); and phenylurethane compounds produced through urethanation with an aniline derivative or with an alkyl-substituted aniline in which the number of carbon atoms constituting the alkyl group is smaller than 8 (Can. Pat. Appl. 2215585, Mar. 17, 1998).

Most amino compounds that have been heretofore used in production of urethane compounds are aniline derivatives and peptide derivatives. As opposed to these, there is no example of using amino compounds having a long-chain alkyl group in production of phenylurethanes. The reason is because the amino compounds of that type are poorly soluble in organic solvents, and do not disperse in reaction liquids, and therefore their reaction efficiency is low.

Despite the situation, however, phenylurethane compounds, if readily obtained from such amino compounds having a long-chain alkyl group on an industrial scale, will be useful.

On the other hand, for producing urea compounds, for example, one general method heretofore known in the art comprises reacting a chloroformate, carbamoyl chloride, phosgene, isocyanate or isothiocyanate with a suitable amino compound. It applies also to producing asymmetric urea compounds.

Most amino compounds that have been heretofore used in production of urea compounds are aniline derivatives and peptide derivatives. As opposed to these, there is no example of using amino compounds having a long-chain alkyl group in production of asymmetric urea compounds. The reason is because the amino compounds of that type are poorly soluble in organic solvents, and do not disperse in reaction liquids, and therefore their reaction efficiency is low.

Despite the situation, however, asymmetric urea compounds, if readily obtained from such amino compounds having a long-chain alkyl group on an industrial scale, will be useful.

Diazo compounds have an extremely high chemical activity, and they react readily with phenol derivatives and active methylene-having compounds that are generally referred to as couplers to form azo dyes. In addition, as sensitive to light, they decompose when exposed to light, and lose their activity. Accordingly, diazo compounds have been used for many years for optical recording materials, for example, typically for optical recording materials such as typically diazo copies (see *Principles of Photographic Science and Engineering*—Nonsilver Photography, edited by the Photographic Society of Japan, published by Corona Publishing CO., LTD., 1982, pp. 89–117, pp. 182–201).

These days, in addition, diazo compounds are applied also to recording materials that require image fixation, as they have the property of decomposing through exposure to light to lose their activity. One typical example is a photo-fixing, thermal recording material in which the recording layer contains a diazo compound and a coupler that are reacted under heat in accordance with an image signal applied thereto to thereby form the intended image and the image is then fixed through exposure to light (Koji Sato et al., *the Journal of the Imaging Electronics Society of Japan*, Vol. 11, No. 4, 1982, pp. 290–296).

However, in the recording materials of the type that contain a diazo compound serving as a color-forming component therein, the chemical activity of the diazo compound is extremely high, and the diazo compound therein gradually decomposes under heat even in the dark to lose its activity. Therefore, the drawback of the recording materials is that their shelf life is short. Various methods have heretofore been proposed for improving the stability of such diazo compounds. One of the most effective methods is to encapsulate a diazo compound into microcapsules.

Encapsulated in microcapsules, the diazo compound is isolated from water and bases that promote the decomposition of the compound. In that condition, therefore, the diazo compound is almost completely prevented from being decomposed, and the shelf life of recording materials that contain the diazo compound in microcapsules is significantly prolonged (Tomomasa Usami et al., *The Journal of the Electrophotography Society of Japan*, Vol. 26, No. 2, 1987, pp. 115–125).

One general method for encapsulating a diazo compound into microcapsules is as follows: A diazonium salt is dissolved in a hydrophobic solvent (to form an oily phase), and this is added to an aqueous solution of a water-soluble polymer (aqueous phase), and emulsified and dispersed by the use of a homogenizer or the like. In the process, a monomer or a prepolymer to form microcapsule walls is added to either one or both of the oily phase and the aqueous phase so that it is polymerized in the interface between the oily phase and the aqueous phase to form a polymer wall around each emulsified particle of the diazonium salt to thereby encapsulate the diazonium salt into the thus-formed microcapsules.

The details of the method are described, for example, in Tomoji Kondo's *Microcapsules* (by Nikkan Kogyo Shinbun, 1970) and Tamotsu Kondo et al's *Microcapsules* (by Sankyo Publishing, 1977). For the microcapsule walls to be formed, various compounds are usable, including for example, crosslinked gelatin, alginates, celluloses, urea resins, urethane resins, melamine resins, and nylon resins.

In cases where microcapsule walls are made of urea resin or urethane resin that undergoes phase transition at its glass transition point and where the glass transition point of the microcapsule walls is higher than room temperature to some extent, the microcapsule walls are impervious to substances at room temperature but are pervious thereto at temperatures not lower than their glass transition point. Therefore, the microcapsules of the type are referred to as thermo-responsive microcapsules, and these are useful in thermal recording materials.

Specifically, a recording material having, on a support, a thermal recording layer that contains thermo-responsive microcapsules with a diazonium salt therein and contains a coupler and a base ensures long-term stability of the diazonium salt therein. When exposed to heat, it readily forms a color image thereon, and when exposed to light, the color image formed is fixed on it. As in the above, the technique of encapsulating a diazo compound into microcapsules makes it possible to significantly improve the stability of the diazo compound therein.

On the other hand, 4-substituted amino-2-alkoxybenzenediazonium salts are especially favorable for color-forming components of thermal recording materials (JP-A No. 4-59288). It is known that they form red dyes of good color quality when coupled with barbituric acid derivatives (JP-A No. 4-197782).

However, the drawbacks with recording materials that contain such a 4-substituted amino-2-alkoxybenzenediazonium salt are that their raw-stock storability (indicating their background stain resistance in storage before they are processed for image formation) and their color image storability (indicating the lightfastness of color images formed on them) are both poor.

SUMMARY OF THE INVENTION

The present invention is to solve the problems in the conventional production methods noted above, and its objects are to provide phenylurethane compounds having a long-chain alkyl group; to provide methods for producing the phenylurethane compounds, which start from an amino compound having a long-chain alkyl group; to provide asymmetric urea compounds having a long-chain alkyl group; to provide methods for producing the asymmetric urea compounds, which start from an amino compound having a long-chain alkyl group and include a step of forming the phenylurethane compound as an intermediate; to provide barbituric acid derivatives having a specific substituent, which are produced from the asymmetric urea compounds and are useful in thermal recording materials; and to provide a diazo thermal recording material which contains the barbituric acid derivative and has good raw-stock storability and good image storability.

One object of the present invention is attained by using a long-chain alkyl group-having amino compound as one starting component to be reacted with a phenoxycarbonyl derivative in the presence of a base in an aqueous solvent. Another object thereof is attained by using a long-chain alkyl group-having amino compound as one starting component to be reacted with a phenylurethane compound in the presence of a base in an organic solvent. Still another object thereof is attained by using, in a diazo thermal recording material, a specific substituent-having diazo compound along with a specific substituent-having barbituric acid derivative that is produced from an asymmetric urea compound and serves as a coupling component therein.

Concretely, the objects of the present invention are attained as follows.

In its first aspect, the present invention provides a phenylurethane compound comprising a molecular structure corresponding to the following general formula (1):

General formula (1)

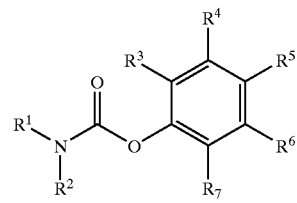

wherein $R^1$ represents an alkyl group having from 8 to 30 carbon atoms in total or an aralkyl group having from 8 to 30 carbon atoms in total; $R^2$ represents a hydrogen atom or an alkyl group; $R^1$ and $R^2$ may be bonded to each other to form a ring; $R^3$, $R^4$ $R^5$, $R^6$ and $R^7$ each independently represent a hydrogen atom, a halogen atom, an alkoxy group, an aryloxy group, a carbonyl derivative group, or a nitro group.

In its second aspect, the present invention provides a phenylurethane compound comprising a molecular structure corresponding to the following general formula (2):

General formula (2)

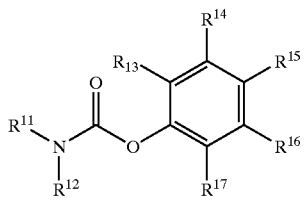

wherein $R^{11}$ represents an unsubstituted alkyl group having from 8 to 30 carbon atoms in total, an unsubstituted aralkyl group having from 8 to 30 carbon atoms in total, an alkoxycarbonylmethyl group having from 8 to 30 carbon atoms in total, an aryloxycarbonylmethyl group having from 8 to 30 carbon atoms in total, an alkoxycarbonylethyl group having from 8 to 30 carbon atoms in total, an aryloxycarbonylethyl group having from 8 to 30 carbon atoms in total, or a carbamoylmethyl group; $R^{12}$ represents a hydrogen atom or an alkyl group; $R^{11}$ and $R^{12}$ may be bonded to each other to form a ring; $R^{13}$, $R^{14}$, $R^{15}$, $R^{16}$ and $R^{17}$ each independently represent a hydrogen atom, a halogen atom, an alkoxy group, an aryloxy group, a carbonyl derivative group, or a nitro group.

In its third aspect, the present invention provides a phenylurethane compound comprising a molecular structure corresponding to the following general formula (3):

General formula (3)

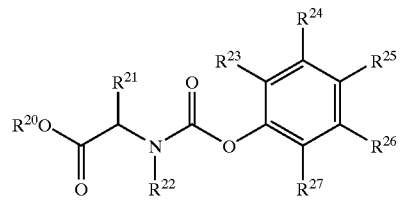

wherein $R^{20}$ represents an alkyl group having from 6 to 30 carbon atoms in total, or an aralkyl group having from 6 to 30 carbon atoms in total; $R^{21}$ represents a hydrogen atom, an alkyl group or an aralkyl group; $R^{22}$ represents a hydrogen atom or an alkyl group; $R^{23}$, $R^{24}$, $R^{25}$, $R^{26}$ and $R^{27}$ each independently represent a hydrogen atom, a halogen atom, an alkoxy group, an aryloxy group, a carbonyl derivative group, or a nitro group.

The present invention also provides methods for producing the phenylurethane compounds. In its first aspect, the present invention provides the method for producing the phenylurethane compound comprising the steps of: (a) adding a base to an aqueous solvent; (b) adding to the aqueous solvent an amino compound of the following general formula General formula (4)

in which $R^{31}$ represents an alkyl group having from 8 to 30 carbon atoms in total or an aralkyl group having from 8 to 30 carbon atoms in total, and $R^{32}$ represents a hydrogen atom or an alkyl group; (c) adding to the aqueous solvent a phenoxycarbonyl derivative of the following general formula (5):

General formula (5)

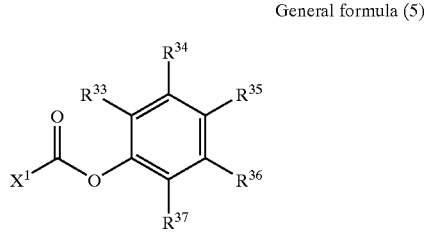

in which $R^{33}$, $R^{34}$, $R^{35}$, $R^{36}$ and $R^{37}$ each independently represent a hydrogen atom, a halogen atom, an alkoxy group, an aryloxy group, a carbonyl derivative group, or a nitro group, and $X^1$ represents a halogen atom, an imidazolyl group or a tetrazolyl group; and (d) allowing the amino compound and the phenoxycarbonyl derivative to react to form a phenylurethane compound of the following general formula (1):

General formula (1)

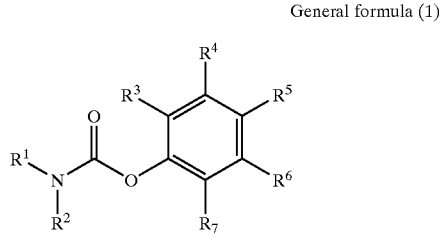

wherein $R^1$ represents an alkyl group having from 8 to 30 carbon atoms in total or an aralkyl group having from 8 to 30 carbon atoms in total; $R^2$ represents a hydrogen atom or an alkyl group; $R^1$ and $R^2$ may be bonded to each other to form a ring; and $R^3$, $R^4$, $R^5$, $R^6$ and $R^7$ each independently represent a hydrogen atom, a halogen atom, an alkoxy group, an aryloxy group, a carbonyl derivative group, or a nitro group.

In its second aspect, the present invention provides the method for producing the phenylurethane compound comprising the steps of: (a) adding a base to an aqueous solvent; (b) adding to the aqueous solvent an amino compound of the following general formula (6):

General formula (6)

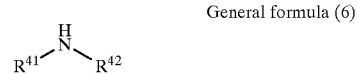

wherein $R^{41}$ represents an unsubstituted alkyl group having from 8 to 30 carbon atoms in total, an unsubstituted aralkyl group having from 8 to 30 carbon atoms in total, an alkoxycarbonylmethyl group having from 8 to 30 carbon atoms in total, an aryloxycarbonylmethyl group having from 8 to 30 carbon atoms in total, an alkoxycarbonylethyl group having from 8 to 30 carbon atoms in total, an aryloxycarbonylethyl group having from 8 to 30 carbon atoms in total, or a carbamoylmethyl group, and $R^{42}$ represents a hydrogen atom or an alkyl group; (c) adding to the aqueous solvent a phenoxycarbonyl derivative of the following general formula (7):

General formula (7)

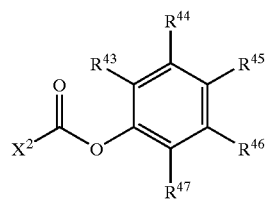

wherein $R^{43}$, $R^{44}$, $R^{45}$, $R^{46}$ and $R^{47}$ each independently represent a hydrogen atom, a halogen atom, an alkoxy group, an aryloxy group, a carbonyl derivative group, or a nitro group, and $X^2$ represents a halogen atom, an imidazolyl group or a tetrazolyl group; and (d) allowing the amino compound and the phenoxycarbonyl derivative to react to form a phenylurethane compound of the following general formula (2):

General formula (2)

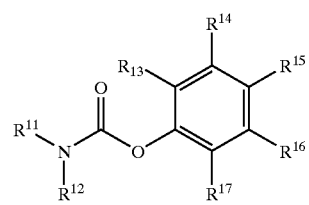

wherein $R^{11}$ represents an unsubstituted alkyl group having from 8 to 30 carbon atoms in total, an unsubstituted aralkyl group having from 8 to 30 carbon atoms in total, an alkoxycarbonylmethyl group having from 8 to 30 carbon atoms in total, an aryloxycarbonylmethyl group having from 8 to 30 carbon atoms in total, an alkoxycarbonylethyl group having from 8 to 30 carbon atoms in total, an aryloxycarbonylethyl group having from 8 to 30 carbon atoms in total, or a carbamoylmethyl group; $R^{12}$ represents a hydrogen atom or an alkyl group; $R^{11}$ and $R^{12}$ may be bonded to each other to form a ring; and $R^{13}$, $R^{14}$, $R^{15}$, $R^{16}$ and $R^{17}$ each independently represent a hydrogen atom, a halogen atom, an alkoxy group, an aryloxy group, a carbonyl derivative group, or a nitro group.

In its third aspect, the present invention provides the method for producing the phenylurethane compound comprising the steps of: (a) adding a base to an aqueous solvent;

(b) adding to the aqueous solvent an amino compound of the following general formula (8):

General formula (8)

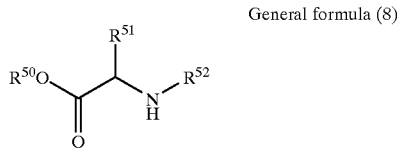

wherein $R^{50}$ represents an alkyl group having from 6 to 30 carbon atoms in total or an aralkyl group having from 6 to 30 carbon atoms in total, $R^{51}$ represents a hydrogen atom, an alkyl group or an aralkyl group, and $R^{52}$ represents a hydrogen atom or an alkyl group; (c) adding to the aqueous solvent a phenoxycarbonyl derivative of the following general formula (9):

General formula (9)

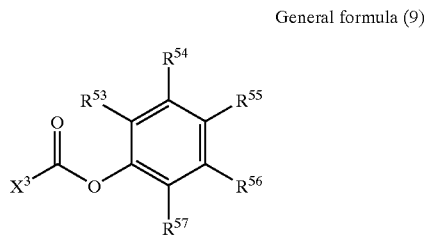

wherein $R^{53}$, $R^{54}$, $R^{55}$, $R^{56}$ and $R^{57}$ each independently represent a hydrogen atom, a halogen atom, an alkoxy group, an aryloxy group, a carbonyl derivative group, or a nitro group, and $X^3$ represents a halogen atom, an imidazolyl group or a tetrazolyl group; and (d) allowing the amino compound and the phenoxycarbonyl derivative to react to form a phenylurethane compound of the following general formula (3):

General formula (3)

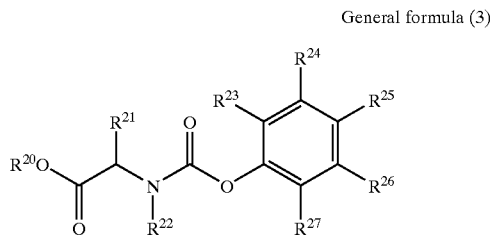

wherein $R^{20}$ represents an alkyl group having from 6 to 30 carbon atoms in total or an aralkyl group having from 6 to 30 carbon atoms in total; $R^{21}$ represents a hydrogen atom, an alkyl group or an aralkyl group; $R^{22}$ represents a hydrogen atom or an alkyl group; and $R^{23}$, $R^{24}$, $R^{25}$, $R^{26}$ and $R^{27}$ each independently represent a hydrogen atom, a halogen atom, an alkoxy group, an aryloxy group, a carbonyl derivative group, or a nitro group.

Subsidiary to the first aspect thereof, the fourth aspect of the present invention provides the method for producing the phenylurethane compound, wherein, during the step of allowing the amino compound and the phenoxycarbonyl derivative to react, a reaction temperature is from 0 to 100° C.; wherein the step of adding the amino compound comprises adding the amino compound to the aqueous solvent in a reaction concentration of from 0.5 to 4.0 mols/liter; and wherein the step of adding the phenoxycarbonyl derivative comprises adding the phenoxycarbonyl derivative in an amount of from 0.8 to 2.0 equivalents per equivalent of the amino compound.

Subsidiary to the second aspect thereof, the fifth aspect of the present invention provides the method for producing the phenylurethane compound, wherein, during the step of allowing the amino compound and the phenoxycarbonyl derivative to react, a reaction temperature is from 0 to 100° C.; wherein the step of adding the amino compound comprises adding the amino compound to the aqueous solvent in a reaction concentration of from 0.5 to 4.0 mols/liter; and wherein the step of adding the phenoxycarbonyl derivative comprises adding the phenoxycarbonyl derivative in an amount of from 0.8 to 2.0 equivalents per equivalent of the amino compound.

Subsidiary to the third aspect thereof, the sixth aspect of the present invention provides the method for producing the phenylurethane compound, wherein, during the step of allowing the amino compound and the phenoxycarbonyl derivative to react, a reaction temperature is from 0 to 100° C.; wherein the step of adding the amino compound comprises adding the amino compound to the aqueous solvent in a reaction concentration of from 0.5 to 4.0 mols/liter; and wherein the step of adding the phenoxycarbonyl derivative comprises adding the phenoxycarbonyl derivative in an amount of from 0.8 to 2.0 equivalents per equivalent of the amino compound.

The present invention also provides asymmetric urea compounds. In its first aspect, the present invention provides an asymmetric urea compound comprising a molecular structure corresponding to the following general formula (10):

General formula (10)

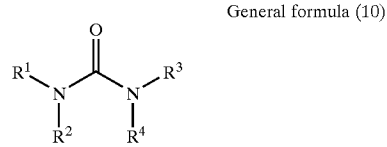

wherein $R^1$ and $R^3$ each independently represent an alkyl group having from 8 to 30 carbon atoms in total or an aralkyl group having from 8 to 30 carbon atoms in total; $R^2$ and $R^4$ each independently represent a hydrogen atom or an alkyl group; and the combination of substituents $R^1$ and $R^2$ differs from the combination of substituents $R^3$ and $R^4$.

In its second aspect, the present invention provides an asymmetric urea compound comprising a molecular structure corresponding to the following general formula (11):

General formula (11)

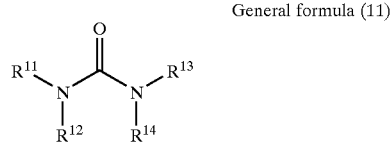

wherein $R^{11}$ and $R^{13}$ each independently represent an unsubstituted alkyl group having from 8 to 30 carbon atoms in total, an unsubstituted aralkyl group having from 8 to 30 carbon atoms in total, an alkoxycarbonylmethyl group having from 8 to 30 carbon atoms in total, an aryloxycarbonylmethyl group having from 8 to 30 carbon atoms in total, an alkoxycarbonylethyl group having from 8 to 30 carbon atoms in total, an aryloxycarbonylethyl group having from 8 to 30 carbon atoms in total, or a carbamoylmethyl group; $R^{12}$ and $R^{14}$ each independently represent a hydrogen atom or an alkyl group; and the combination of substituents $R^{11}$ and $R^{12}$ differs from the combination of substituents $R^{13}$ and $R^{14}$.

The present invention also provides methods for producing the asymmetric urea compounds. In its first aspect, the present invention provides the method for producing the asymmetric urea compound comprising the steps of: (a) adding a base to an organic solvent; (b) adding to the organic solvent a phenylurethane compound of the following general formula (12):

General formula (12)

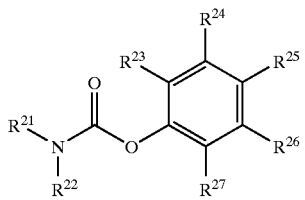

wherein $R^{21}$ represents an alkyl group having from 8 to 30 carbon atoms in total or an aralkyl group having from 8 to 30 carbon atoms in total, $R^{22}$ represents a hydrogen atom or an alkyl group, $R^{23}$, $R^{24}$, $R^{25}$, $R^{26}$ and $R^{27}$ each independently represent a hydrogen atom, a halogen atom, an alkoxy group, an aryloxy group, a carbonyl derivative group, or a nitro group, and the combination of substituents $R^{21}$ and $R^{22}$ differs from the combination of substituents $R^{28}$ and $R^{29}$ of the following general formula (13); (c) adding to the organic solvent an amino compound of the following general formula (13):

General formula (13)

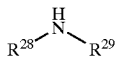

wherein $R^{28}$ represents an alkyl group having from 8 to 30 carbon atoms in total or an aralkyl group having from 8 to 30 carbon atoms in total, and $R^{29}$ represents a hydrogen atom or an alkyl group, and $R^{28}$ and $R^{29}$ differs from the combination of substituents $R^{21}$ and $R^{22}$ of the general formula (12); and (d) allowing the phenylurethane compound and the amino compound to react to form an asymmetric urea compound of the following general formula (10):

General formula (10)

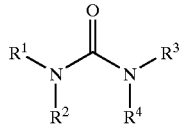

wherein $R^1$ and $R^3$ each independently represent an alkyl group having from 8 to 30 carbon atoms in total or an aralkyl group having from 8 to 30 carbon atoms in total; $R^2$ and $R^4$ each independently represent a hydrogen atom or an alkyl group; and the combination of substituents $R^1$ and $R^2$ differs from the combination of substituents $R^3$ and $R^4$.

In its second aspect, the present invention provides the method for producing the asymmetric urea compound comprising the steps of: (a) adding a base to an organic solvent; (b) adding to the organic solvent a phenylurethane compound of the following general formula (14):

General formula (14)

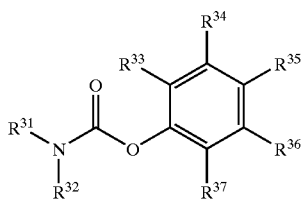

wherein $R^{31}$ represents an unsubstituted alkyl group having from 8 to 30 carbon atoms in total, an unsubstituted aralkyl group having from 8 to 30 carbon atoms in total, an alkoxycarbonylmethyl group having from 8 to 30 carbon atoms in total, an aryloxycarbonylmethyl group having from 8 to 30 carbon atoms in total, an alkoxycarbonylethyl group having from 8 to 30 carbon atoms in total, an aryloxycarbonylethyl group having from 8 to 30 carbon atoms in total, or a carbamoylmethyl group, $R^{32}$ represents a hydrogen atom or an alkyl group, $R^{33}$, $R^{34}$, $R^{35}$, $R^{36}$ and $R^{37}$ each independently represent a hydrogen atom, a halogen atom, an alkoxy group, an aryloxy group, a carbonyl derivative group, or a nitro group, and the combination of substituents $R^{31}$ and $R^{32}$ differs from the combination of substituents $R^{38}$ and $R^{39}$ of the following general formula (15); and (c) adding to the organic solvent an amino compound of the following general formula (15):

General formula (15)

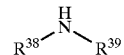

wherein $R^{38}$ represents an unsubstituted alkyl group having from 8 to 30 carbon atoms in total, an unsubstituted aralkyl group having from 8 to 30 carbon atoms in total, an alkoxycarbonylmethyl group having from 8 to 30 carbon atoms in total, an aryloxycarbonylmethyl group having from 8 to 30 carbon atoms in total, an alkoxycarbonylethyl group having from 8 to 30 carbon atoms in total, an aryloxycarbonylethyl group having from 8 to 30 carbon atoms in total, or a carbamoylmethyl group, $R^{39}$ represents a hydrogen atom or an alkyl group, and $R^{38}$ and $R^{39}$ differs from the combination of substituents $R^{31}$ and $R^{32}$ of the general formula (14); and (d) allowing the phenylurethane compound and the amino compound to react to form an asymmetric urea compound of the following general formula (11):

General formula (11)

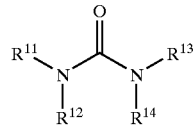

wherein $R^{11}$ and $R^{13}$ each independently represent an unsubstituted alkyl group having from 8 to 30 carbon atoms in total, an unsubstituted aralkyl group having from 8 to 30 carbon atoms in total, an alkoxycarbonylmethyl group having from 8 to 30 carbon atoms in total, an aryloxycarbonylmethyl group having from 8 to 30 carbon atoms in total, an alkoxycarbonylethyl group having from 8 to 30 carbon atoms in total, an aryloxycarbonylethyl group having from 8 to 30 carbon atoms in total, or a carbamoylmethyl group; $R^{12}$ and $R^{14}$ each independently represent a hydrogen atom or an alkyl group; and the combination of substituents $R^{11}$ and $R^{12}$ differs from the combination of substituents $R^{13}$ and $R^{14}$.

Subsidiary to the first aspect thereof, the third aspect of the present invention provides the method for producing the asymmetric urea compound, wherein, during the step of allowing the amino compound and the phenylurethane compound to react, a reaction temperature is from 50 to 110° C.; wherein the step of adding the phenylurethane compound comprises adding the phenylurethane compound to the aqueous solvent in a reaction concentration of from 0.2 to 5.0 mols/liter; and wherein the step of adding the amino compound comprises adding the amino compound in an amount of from 0.8 to 5.0 equivalents per equivalent of the phenylurethane compound.

Subsidiary to the second aspect thereof, the fourth aspect of the present invention provides the method for producing the asymmetric urea compound, wherein, during the step of allowing the amino compound and the phenylurethane compound to react, a reaction temperature is from 50 to 110° C.; wherein the step of adding the phenylurethane compound comprises adding the phenylurethane compound to the aqueous solvent in a reaction concentration of from 0.2 to 5.0 mols/liter; and wherein the step of adding the amino compound comprises adding the amino compound in an amount of from 0.8 to 5.0 equivalents per equivalent of the phenylurethane compound.

The present invention also provides barbituric acid derivatives. In its first aspect, the present invention provides a barbituric acid derivative comprising a molecular structure corresponding to the following general formula (18):

General formula (18)

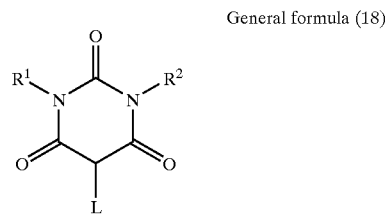

wherein $R^1$ and $R^2$ each represent an optionally-substituted alkyl group or an optionally-substituted aralkyl group; $R^1$ and $R^2$ are different from each other; and L represents a hydrogen atom, or a substituent capable of leaving the barbituric acid derivative when the barbituric acid derivative is coupled with a diazo compound.

Subsidiary to the first aspect thereof, the second aspect of the present invention provides the barbituric acid derivative comprising a molecular structure corresponding to the following general formula (19):

General formula (19)

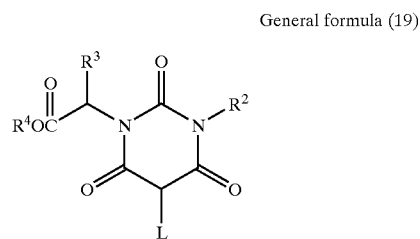

wherein $R^3$ represents a hydrogen atom, an optionally-substituted alkyl group, or an optionally-substituted aralkyl group; $R^4$ represents an optionally-substituted alkyl group or an optionally-substituted aralkyl group; and $R^3$ is independent of $R^4$.

Subsidiary to the second aspect thereof, the third aspect of the present invention provides the barbituric acid derivative comprising a molecular structure corresponding to the following general formula (20):

General formula (20)

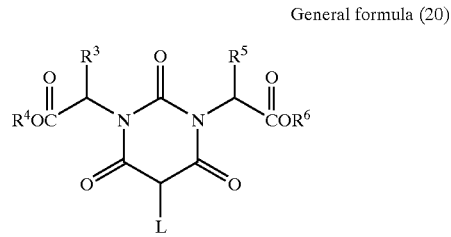

wherein $R^5$ represents a hydrogen atom, an optionally-substituted alkyl group, or an optionally-substituted aralkyl group; $R^6$ represents an optionally-substituted alkyl group or an optionally-substituted aralkyl group; and $R^5$ is independent of $R^6$.

The present invention also provides a diazo thermal recording material comprising a support and a thermal recording layer disposed on the support, the recording layer including a diazo compound, a coupling component and an organic base. In its first aspect, the present invention provides the diazo thermal recording material, in which the coupling component includes at least one barbituric acid derivative comprising a molecular structure corresponding to the following general formula (18):

General formula (18)

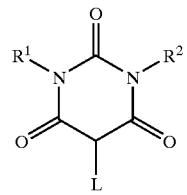

wherein $R^1$ and $R^2$ each represent an optionally-substituted alkyl group or an optionally-substituted aralkyl group; $R^1$ and $R^2$ are different from each other; and L represents a hydrogen atom, or a substituent capable of leaving the barbituric acid derivative when the barbituric acid derivative is coupled with a diazo compound.

Subsidiary to the first aspect thereof, the second aspect of the present invention provides the diazo thermal recording material, in which the coupling component includes at least one barbituric acid derivative comprising a molecular structure corresponding to the following general formula (19):

General formula (19)

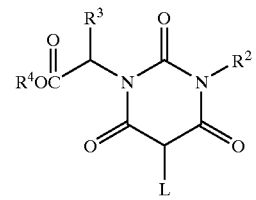

wherein $R^3$ represents a hydrogen atom, an optionally-substituted alkyl group, or an optionally-substituted aralkyl group; $R^4$ represents an optionally-substituted alkyl group or an optionally-substituted aralkyl group; and $R^3$ is independent of $R^4$.

Subsidiary to the first aspect thereof, the third aspect of the present invention provides the diazo thermal recording material, in which the coupling component includes at least one barbituric acid derivative comprising a molecular structure corresponding to the following general formula (20):

General formula (20)

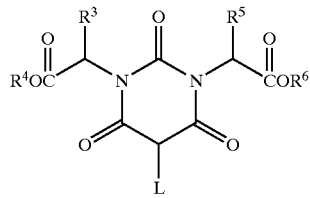

wherein $R^5$ represents a hydrogen atom, an optionally-substituted alkyl group, or an optionally-substituted aralkyl group; $R^6$ represents an optionally-substituted alkyl group or an optionally-substituted aralkyl group; and $R^5$ is independent of $R^6$.

Subsidiary to the first aspect thereof, the fourth aspect of the present invention provides the diazo thermal recording material, in which the diazo compound includes at least one compound comprising a molecular structure corresponding to the following general formula (21):

General formula (21)

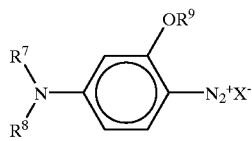

wherein $R^7$, $R^8$ and $R^9$ each independently represent an optionally-substituted alkyl group or an optionally-substituted aryl group; and X represents an anion.

Subsidiary to the first aspect thereof, the fifth aspect of the present invention provides the diazo thermal recording material, in which the diazo compound is encapsulated in microcapsules.

DESCRIPTION OF THE PREFERRED EMBODIMENTS

Phenylurethane compounds and methods for producing them:

The phenylurethane compounds of the present invention have a long-chain alkyl group; and in the methods for producing them, a phenoxycarbonyl derivative is reacted with an amino compound having a long-chain alkyl group in the molecule.

The phenylurethane compounds and their production methods of the present invention are described.

Phenylurethane Compounds

The phenylurethane compounds of the present invention are represented by the following general formula (1):

General formula (1)

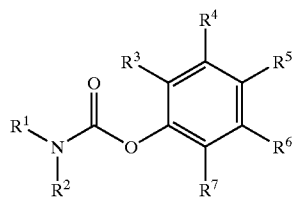

In general formula (1), $R^1$ represents an alkyl group having from 8 to 30 carbon atoms in total, or an aralkyl group having from 8 to 30 carbon atoms in total.

The alkyl group having from 8 to 30 carbon atoms in total may be substituted or unsubstituted, including, for example, octyl, dodecyl, octadecyl, 3-dodecyloxypropyl, hexyloxycarbonylmethyl, octyloxycarbonylmethyl, dodecyloxycarbonylmethyl, decylaminocarbonylmethyl, dodecanesulfonylbenzyl and N-butylaminopropyl groups. Of those, preferred are alkyl groups each having from 8 to 20 carbon atoms in total.

The substituent for the optionally-substituted alkyl group includes, for example, an ester group, an ether group, a thioether group, a carbonyl derivative group, a cyano group, a carbamoyl group, a sulfamoyl group, and a urea group. Of those, preferred are an ester group, an ether group, and a carbamoyl group.

The aralkyl group having from 8 to 30 carbon atoms in total may be substituted or unsubstituted, including, for example, dodecylbenzyl, hexadecylbenzyl, dimethylbenzyl, octyloxybenzyl and octadecylaminocarbonylbenzyl groups. Of those, preferred are aralkyl groups each having from 8 to 20 carbon atoms in total. For the substituents for the optionally-substituted aralkyl group and for their preferred examples, referred to are those of the optionally-substituted alkyl group mentioned hereinabove for $R^1$.

In general formula (1), $R^2$ represents a hydrogen atom or an alkyl group.

The alkyl group for $R^2$ may be substituted or unsubstituted, preferably having from 1 to 20 carbon atoms in total. Preferable examples thereof include methyl, ethyl, propyl, hexyl, octyl and dodecyl groups. Of those, more preferred are alkyl groups each having from 1 to 10 carbon atoms in total; even more preferred are alkyl groups each having from 1 to 8 carbon atoms in total; and especially preferred is an octyl group. For the substituents for the optionally-substituted alkyl group and for their preferred examples, referred to are those mentioned hereinabove for $R^1$.

Preferably, $R^2$ is a hydrogen atom.

In general formula (1), $R^1$ and $R^2$ may be bonded to each other to form a ring. The ring to be formed by them includes, for example, 5-membered, 6-membered, 8-membered and 12-membered rings.

In general formula (1), $R^3$, $R^4$, $R^5$, $R^6$ and $R^7$ each independently represent a hydrogen atom, a halogen atom, an alkoxy group, an aryloxy group, a carbonyl derivative group, or a nitro group.

The halogen atom for $R^3$ to $R^7$ includes, for example, fluorine, chlorine, bromine and iodine atoms.

The alkoxy group for $R^3$ to $R^7$ may be substituted or unsubstituted, preferably having from 1 to 30 carbon atoms in total. Examples thereof include methoxy, ethoxy, butoxy, hexyloxy, octyloxy, dodecyloxy and octadecyloxy groups. Of those, more preferred are alkoxy groups each having from 1 to 20 carbon atoms in total; even more preferred are alkoxy groups each having from 1 to 8 carbon atoms in total; and especially preferred are methoxy, ethoxy and octyloxy groups.

The aryloxy group for $R^3$ to $R^7$ may be substituted or unsubstituted, preferably having from 6 to 30 carbon atoms in total. Examples thereof include phenoxy, methylphenoxy, dodecylphenoxy and dimethoxyphenoxy groups. Of those, more preferred are aryloxy groups each having from 6 to 20 carbon atoms in total; and even more preferred are aryloxy groups each having from 6 to 8 carbon atoms in total.

The carbonyl derivative group for $R^3$ to $R^7$ may be substituted or unsubstituted, including, for example, an alkylcarbonyl group having from 2 to 9 carbon atoms in total, and an arylcarbonyl group having from 7 to 15 carbon atoms in total.

The alkylcarbonyl group having from 2 to 9 carbon atoms in total includes, for example, methylcarbonyl, ethylcarbonyl, propylcarbonyl, butylcarbonyl, hexylcarbonyl and octylcarbonyl groups. Of those, preferred are alkylcarbonyl groups each having from 2 to 7 carbon atoms in total.

The arylcarbonyl group having from 7 to 15 carbon atoms in total includes, for example, phenylcarbonyl, methylphenylcarbonyl, ethylphenylcarbonyl, propylphenylcarbonyl, butylphenylcarbonyl, hexylphenylcarbonyl and octylphenylcarbonyl groups. Of those, preferred are arylcarbonyl groups each having from 7 to 12 carbon atoms in total.

For the substituents for the optionally-substituted alkoxy, aryloxy and carbonyl derivative groups for $R^3$ to $R^7$, and for their preferred examples, referred to are those mentioned hereinabove for the substituents for $R^1$.

For $R^3$ to $R^7$, preferred are a hydrogen atom, a halogen atom and a nitro group.

Of the phenylurethane compounds of general formula (1), preferred are those of the following general formula (2):

General formula (2)

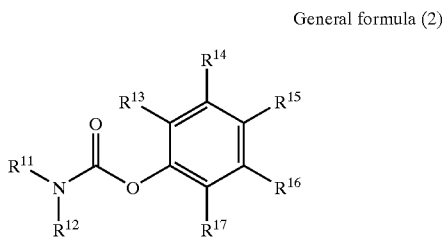

In general formula (2), $R^{11}$ represents an unsubstituted alkyl group having from 8 to 30 carbon atoms in total, an unsubstituted aralkyl group having from 8 to 30 carbon atoms in total, an alkoxycarbonylmethyl group having from 8 to 30 carbon atoms in total, an aryloxycarbonylmethyl group having from 8 to 30 carbon atoms in total, an alkoxycarbonylethyl group having from 8 to 30 carbon atoms in total, an aryloxycarbonylethyl group having from 8 to 30 carbon atoms in total, or a carbamoylmethyl group.

The meaning of the unsubstituted alkyl group having from 8 to 30 carbon atoms in total for $R^{11}$ is the same as that of the unsubstituted alkyl group for $R^1$ mentioned hereinabove; and the meaning of the unsubstituted aralkyl group having from 8 to 30 carbon atoms in total for $R^{11}$ is the same as that of the unsubstituted aralkyl group for $R^1$ mentioned hereinabove.

In the alkoxycarbonylmethyl group having from 8 to 30 carbon atoms in total for $R^{11}$, the alkoxy moiety may be substituted or unsubstituted, preferably having from 6 to 26 carbon atoms in total. The alkoxycarbonylmethyl group includes, for example, octyloxycarbonylmethyl, decyloxycarbonylmethyl, dodecyloxycarbonylmethyl and octadecyloxycarbonylmethyl groups.

Of those, more preferred are alkoxycarbonylmethyl groups in which the alkoxy moiety has from 6 to 22 carbon atoms in total; even more preferred are alkoxycarbonylmethyl groups in which the alkoxy moiety has from 8 to 18 carbon atoms; and especially preferred are octyloxycarbonylmethyl, decyloxycarbonylmethyl and dodecyloxycarbonylmethyl groups. For the substituents for the optionally-substituted groups and for their preferred examples, referred to are those mentioned hereinabove for the substituents for $R^1$.

In the aryloxycarbonylmethyl group having from 8 to 30 carbon atoms in total for $R^{11}$, the aryl moiety may be substituted or unsubstituted. Preferably, in this, the aryloxy moiety has from 12 to 28 carbon atoms in total. The aryloxycarbonylmethyl group includes, for example, hexylphenoxycarbonylmethyl, octyloxyphenoxycarbonylmethyl, decylsulfonylphenoxycarbonylmethyl, octylaminocarbonylphenoxycarbonylmethyl and dodecyloxycarbonylphenoxycarbonylmethyl groups.

Of those, more preferred are aryloxycarbonylmethyl groups in which the aryloxy moiety has from 12 to 22 carbon atoms in total; even more preferred are aryloxycarbonylmethyl groups in which the aryloxy moiety has from 14 to 22 carbon atoms; and especially preferred are octyloxyphenoxycarbonylmethyl and decanesulfonylphenoxycarbonylmethyl groups. For the substituents for the optionally-substituted groups and for their preferred examples, referred to are those mentioned hereinabove for the substituents for $R^1$.

In the alkoxycarbonylethyl group having from 8 to 30 carbon atoms in total for $R^{11}$, the alkoxy moiety may be substituted or unsubstituted, preferably having from 5 to 25 carbon atoms in total. The alkoxycarbonylethyl group includes, for example, hexyloxycarbonylethyl, octyloxycarbonylethyl, decyloxycarbonylethyl, dodecyloxycarbonylethyl and octadecyloxycarbonylethyl groups.

Of those, more preferred are alkoxycarbonylethyl groups in which the alkoxy moiety has from 6 to 22 carbon atoms in total; even more preferred are alkoxycarbonylethyl groups in which the alkoxy moiety has from 7 to 18 carbon atoms; and especially preferred are octyloxycarbonylethyl, decyloxycarbonylethyl and dodecyloxycarbonylethyl groups. For the substituents for the optionally-substituted groups and for their preferred examples, referred to are those mentioned hereinabove for the substituents for $R^1$.

In the aryloxycarbonylethyl group having from 8 to 30 carbon atoms in total for $R^{11}$, the aryl moiety may be substituted or unsubstituted. Preferably, in this, the aryloxy moiety has from 12 to 28 carbon atoms in total. The aryloxycarbonylethyl group includes, for example, hexylphenoxycarbonylethyl, octyloxyphenoxycarbonylethyl, decanesulfonylphenoxycarbonylethyl, octylaminocarbonylphenoxycarbonylethyl and dodecyloxycarbonylphenoxycarbonylethyl groups.

Of those, more preferred are aryloxycarbonylethyl groups in which the aryloxy moiety has from 12 to 22 carbon atoms in total; even more preferred are aryloxycarbonylethyl groups in which the aryloxy moiety has from 14 to 22 carbon atoms; and especially preferred are octyloxyphenoxycarbonylethyl and decanesulfonylphenoxycarbonylethyl groups. For the substituents for the optionally-substituted groups and for their preferred examples, referred to are those mentioned hereinabove for the substituents for $R^1$.

In general formula (2), $R^{12}$ represents a hydrogen atom or an alkyl group. The meaning of the alkyl group is the same as that of the alkyl group for $R^2$ in general formula (1) mentioned hereinabove. $R^{11}$ and $R^{12}$ in general formula (2) may be bonded to each other to form a ring. The meaning of the ring to be formed in general formula (2) is the same as that of the ring to be formed by $R^1$ and $R^2$ in general formula (1).

In general formula (2), $R^{13}$, $R^{14}$, $R^{15}$, $R^{16}$ and $R^{17}$ each independently represent a hydrogen atom, a halogen atom, an alkoxy group, an aryloxy group, a carbonyl derivative group, or a nitro group. Their meanings are the same as those of $R^3$, $R^4$, $R^5$, $R^6$ and $R^7$ in general formula (1) mentioned hereinabove.

Of the phenylurethane compounds of general formula (2), more preferred are those of the following general formula (3):

General formula (3)

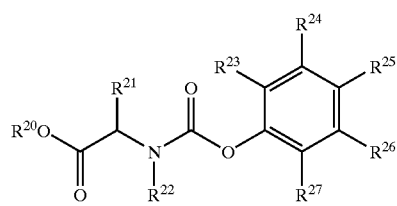

In general formula (3), $R^{20}$ represents an alkyl group having from 6 to 30 carbon atoms in total, or an aralkyl group having from 6 to 30 carbon atoms in total.

The alkyl group having from 6 to 30 carbon atoms in total for $R^{20}$ may be substituted or unsubstituted, preferably having from 6 to 22 carbon atoms in total. Examples thereof include octyl, decyl, dodecyl, tetradecyl, octadecyl and docosyl groups. Of those, more preferred are alkyl groups each having from 8 to 20 carbon atoms in total; more preferred are alkyl groups each having from 8 to 18 carbon atoms in total; and more preferred are octyl, dodecyl and octadecyl groups. For the substituents, if any, for the alkyl group and for their preferred examples, referred to are those mentioned hereinabove for the substituents for $R^1$.

The aralkyl group having from 6 to 30 carbon atoms in total for $R^{20}$ may be substituted or unsubstituted, preferably having from 8 to 22 carbon atoms in total. Examples thereof include hexylbenzyl, octyloxybenzyl, decylsulfonylbenzyl, dihexylbenzyl and dodecyloxyphenylpropyl groups. Of those, more preferred are aralkyl groups each having from 12 to 20 carbon atoms in total; more preferred are aralkyl groups each having from 12 to 18 carbon atoms in total; and even more preferred are octyloxybenzyl and dihexyloxybenzyl groups. For the substituents, if any, for the aralkyl group and for their preferred examples, referred to are those mentioned hereinabove for the substituents for $R^1$.

Of those mentioned above, especially preferred are octyl, decyl, dodecyl and octadecyl groups for $R^{20}$.

In general formula (3), $R^{21}$ represents a hydrogen atom, an allyl group or an aralkyl group. The meaning of the alkyl group is the same as that of the alkyl group for $R^2$ in general formula (1) mentioned hereinabove. The aralkyl group includes, for example, benzyl, methylbenzyl, propylbenzyl, butoxybenzyl, hexylcarbonylbenzyl and octanesulfonylbenzyl groups. For $R^{21}$, especially preferred are a hydrogen atom, and methyl, ethyl and octyl groups.

In general formula (3), $R^{22}$ represents a hydrogen atom or an alkyl group. The meaning of the alkyl group is the same as that of the alkyl group for $R^2$ in general formula (1). For $R^{22}$, preferred are a hydrogen atom, and methyl, ethyl and benzyl groups; and more preferred is a hydrogen atom.

In general formula (3), $R^{23}$, $R^{24}$, $R^{25}$, $R^{26}$ and $R^{27}$ each independently represent a hydrogen atom, a halogen atom, an alkoxy group, an aryloxy group, a carbonyl derivative group, or a nitro group. Their meanings are the same as those of $R^3$, $R^4$, $R^5$, $R^6$ and $R^7$ in general formula (1).

Specific examples of the phenylurethane compounds of general formulae (1) to (3) (Compounds (1) to (20)) are mentioned below, to which, however, the present invention is not limited.

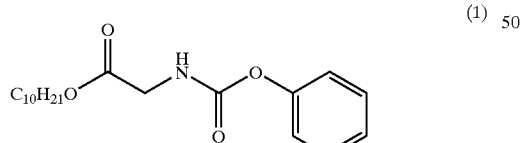

(1)

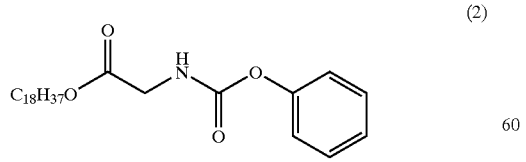

(2)

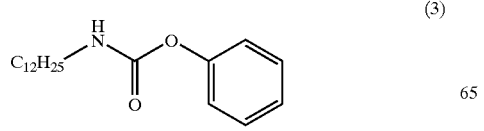

(3)

-continued

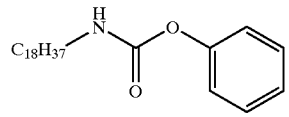

(4)

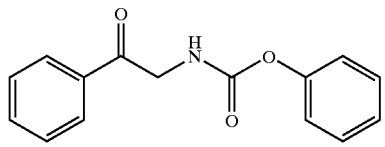

(5)

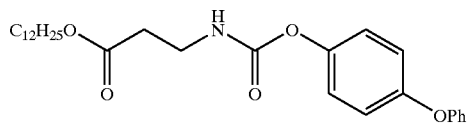

(6)

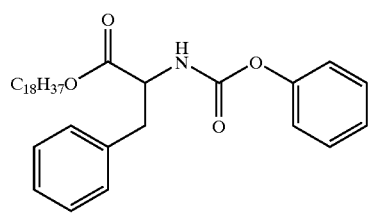

(7)

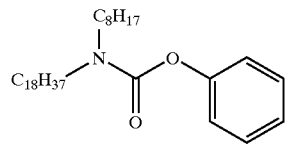

(8)

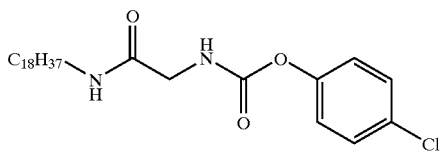

(9)

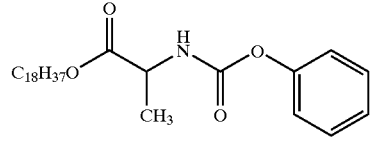

(10)

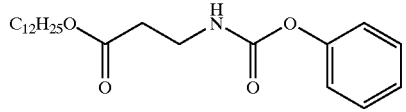

(11)

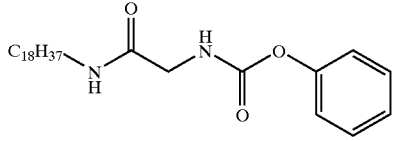

(12)

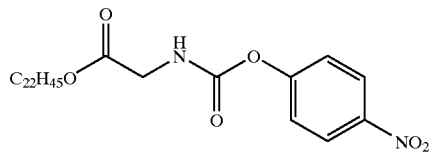

(13)

-continued (14)

$C_{12}H_{25}$—NH—C(=O)—O—[phenyl]—$OC_4H_9$ (15)

$C_{18}H_{37}$—N(CH$_3$)—C(=O)—CH$_2$—NH—C(=O)—O—[phenyl]

(16)

$C_{12}H_{25}O$—[phenyl]—C(=O)—CH$_2$—NH—C(=O)—O—[2,4-dichlorophenyl]

(17)

$C_{12}H_{25}$—[phenyl]—O—CH$_2$CH$_2$—O—CH$_2$—C(=O)—NH—C(=O)—O—[phenyl]

(18)

$C_8H_{17}O$—CH$_2$CH$_2$—NH—C(=O)—O—[phenyl]—COCH$_3$ (19)

$C_{12}H_{25}$—[phenyl]—CH$_2$—O—CH$_2$—C(=O)—NH—C(=O)—O—[phenyl]

(20)

$C_8H_{17}SO_2$—[phenyl]—CH$_2$—NH—C(=O)—O—[phenyl]

Methods for Producing Phenylurethane Compounds

Next described are methods for producing the phenylurethane compounds of the present invention.

The basic reaction mechanism for producing the phenylurethane compounds of the present invention is shown by the following reaction formula:

Reaction Formula $R^{31}$—NH—$R^{32}$ + [phenyl with $R^{33}$, $R^{34}$, $R^{35}$, $R^{36}$, $R^{37}$]—O—C(=O)—$X^1$ →

General formula (4)    General formula (5)

[Phenylurethane Compound with $R^{31}$, $R^{32}$ on N, and $R^{33}$–$R^{37}$ on phenyl]

Phenylurethane Compound

One method for producing the phenylurethane compounds of general formula (1) of the present invention comprises reacting an amino compound of general formula (4) with a phenoxycarbonyl derivative of general formula (5), in the presence of a base in an aqueous solvent (this may optionally contain an organic solvent serving as an auxiliary solvent).

In this method, the long-chain alkyl group-having amino compound can form an emulsion in the aqueous solvent, therefore ensuring good reaction efficiency in the reaction system. Stirring the system is not retarded at all, and the reaction proceeds rapidly.

The reaction is effected in a solvent, and the solvent is an aqueous solvent optionally containing an organic solvent that serves as an auxiliary solvent. The aqueous solvent includes, for example, water such as distilled water or ion-exchanged water, and a mixture of such water and a water-miscible solvent.

Adding an auxiliary solvent to the aqueous solvent makes it easy to stir the reaction system. The organic solvent that serves as the auxiliary solvent includes, for example, chloroform, ethyl acetate, tetrahydrofuran, acetone, methanol, ethanol, hexane, cyclohexane, toluene, acetonitrile and propionitrile. The ratio of the organic solvent to the aqueous solvent that contains the organic solvent preferably is from 10 to 200% by weight, more preferably from 50 to 100% by weight of water in the aqueous solvent.

The reaction of the amino compound with the phenoxycarbonyl derivative is effected in the presence of a base, which promotes the reaction. Preferably, for example, the base is an alkali metal or alkaline earth metal salt. The time in which the base is added to the reaction system may be determined in any desired manner, but is preferably before the starting material, the amino compound and/or the phenoxycarbonyl derivative is added to the aqueous solvent.

The amount of the base preferably is from 0.9 to 4 equivalents, more preferably from 1 to 1.2 equivalents to one equivalent of the phenoxycarbonyl derivative.

The concentration of the amino compound to be reacted with the phenoxycarbonyl derivative preferably is from 0.5 to 4.0 mols/liter, more preferably from 0.5 to 2.0 mols/liter.

If the concentration is smaller than 0.5 mols/liter, that is, if the amount of the amino compound is too small, the reaction will take a lot of time; but if larger than 4.0 mols/liter, that is, if the amount of the amino compound is too large, the reaction system will be difficult to stir.

The amount of the phenoxycarbonyl derivative to be reacted with the amino compound preferably is from 0.8 to 2.0 equivalents, more preferably from 0.8 to 1.2 equivalents to one equivalent of the amino compound.

The reaction temperature preferably is from 0 to 100° C., more preferably from 0 to 50° C., since the solvent, water must be kept liquid in the reaction system under atmospheric pressure.

If the reaction temperature is lower than 0° C., the solubility of the amino compound in the solvent will be low and the reaction speed will be therefore lowered.

The starting materials in the reaction, the amino compound of general formula (4) and the phenoxycarbonyl derivative of general formula (5) are described.

In the reaction, $R^{31}$ in general formula (4) is an alkyl group having from 8 to 30 carbon atoms in total, or an aralkyl group having from 8 to 30 carbon atoms in total, and its meaning is the same as that of $R^1$ in general formula (1) mentioned hereinabove. For the substituents for $R^{31}$, referred to are those for $R^1$ also mentioned hereinabove. $R^{32}$ in general formula (4) is a hydrogen atom or an alkyl group, and its meaning is the same as that of $R^2$ in general formula (1) mentioned hereinabove. For the substituents for $R^{32}$, referred to are those for $R^2$ also mentioned hereinabove.

In the reaction, $R^{33}$, $R^{34}$, $R^{35}$, $R^{36}$ and $R^{37}$ in general formula (5) each independently represent a hydrogen atom, a halogen atom, an alkoxy group, an aryloxy group, a carbonyl derivative group, or a nitro group, and their meanings are the same as those of $R^3$, $R^4$, $R^5$, $R^6$ and $R^7$ in general formula (1) mentioned hereinabove. For the substituents for $R^{33}$, $R^{34}$, $R^{35}$, $R^{36}$ and $R^{37}$, referred to are those for $R^3$, $R^4$, $R^5$, $R^6$ and $R^7$ also mentioned hereinabove.

In general formula (5), $X^1$ is a halogen atom, an imidazolyl group or a tetrazolyl group, but is preferably a halogen atom in view of the reactivity and the cost of the compound.

The groups $R^{31}$ to $R^{37}$ in the reaction product, phenylurethane compound (this is the phenylurethane compound of general formula (1)) correspond to those in general formulae (4) and (5).

The amino compound of general formula (4) and the phenoxycarbonyl derivative of general formula (5) are available on the market or are produced in known methods. The same shall apply also to the compounds of general formulae (6) and (8) and those of general formulae (7) and (9) that are described hereinunder.

For the reaction of the amino compound of general formula (4) with the phenoxycarbonyl derivative of general formula (5), preferred is a method of reacting an amino compound of the following general formula (6) with a phenoxycarbonyl derivative of the following general formula (7). In this case, produced are phenylurethanes of general formula (2) mentioned hereinabove.

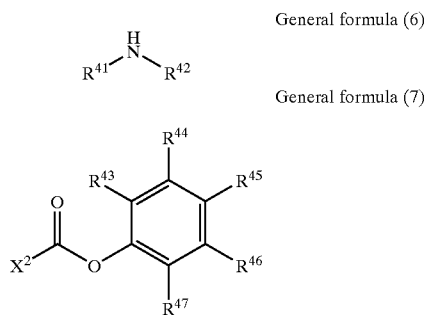

General formula (6)

General formula (7)

In general formula (6), $R^{41}$ is an unsubstituted alkyl group having from 8 to 30 carbon atoms in total, an unsubstituted aralkyl group having from 8 to 30 carbon atoms in total, an alkoxycarbonylmethyl group having from 8 to 30 carbon atoms in total, an aryloxycarbonylmethyl group having from 8 to 30 carbon atoms in total, an alkoxycarbonylethyl group having from 8 to 30 carbon atoms in total, an aryloxycarbonylethyl group having from 8 to 30 carbon atoms in total, or a carbamoylmethyl group, and its meaning is the same as that of $R^{11}$ in general formula (2) mentioned hereinabove. For the substituents for $R^{41}$, referred to are those for $R^{11}$ also mentioned hereinabove. In general formula (6), $R^{42}$ is a hydrogen atom or an alkyl group, and its meaning is the same as that of $R^2$ in general formula (1) mentioned hereinabove. For the substituents for $R^{42}$, referred to are those for $R^2$ also mentioned hereinabove.

In general formula (7), $R^{43}$, $R^{44}$, $R^{45}$, $R^{46}$ and $R^{47}$ each independently represent a hydrogen atom, a halogen atom, an alkoxy group, an aryloxy group, a carbonyl derivative group, or a nitro group, and their meanings are the same as those of $R^3$, $R^4$, $R^5$, $R^6$ and $R^7$ in general formula (1) mentioned hereinabove. For the substituents for $R^{43}$, $R^{44}$, $R^{45}$, $R^{46}$ and $R^{47}$, referred to are those for $R^3$, $R^4$, $R^5$, $R^6$ and $R^7$ also mentioned hereinabove. $X^2$ in general formula (7) is a halogen atom, an imidazolyl group or a tetrazolyl group, but is preferably a halogen atom in view of the reactivity and the cost of the compound.

For the reaction, more preferred is a method of reacting an amino compound of the following general formula (8) with a phenoxycarbonyl derivative of the following general formula (9). In this case, produced are phenylurethanes of general formula (3) mentioned hereinabove.

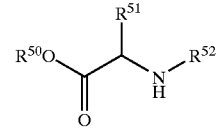

General formula (8)

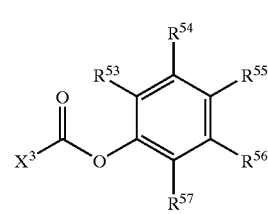

General formula (9)

In general formula (8), $R^{50}$ is an alkyl group having from 6 to 30 carbon atoms in total, or an aralkyl group having from 6 to 30 carbon atoms in total, and its meaning is the same as that of $R^{20}$ in general formula (3) mentioned hereinabove. For the substituents for $R^{50}$, referred to are those for $R^{20}$ also mentioned hereinabove. In general formula (8), $R^{51}$ is a hydrogen atom, an alkyl group or an aralkyl group, and $R^{52}$ is a hydrogen atom or an alkyl group; and their meanings are the same as those of $R^{21}$ and $R^{22}$, respectively, in general formula (3) mentioned hereinabove. For the substituents for $R^{51}$ and $R^{52}$, referred to are those for $R^{21}$ and $R^{22}$ also mentioned hereinabove.

In general formula (9), $R^{53}$, $R^{54}$, $R^{55}$, $R^{56}$ and $R^{57}$ each independently represent a hydrogen atom, a halogen atom, an alkoxy group, an aryloxy group, a carbonyl derivative group, or a nitro group, and their meanings are the same as those of $R^3$, $R^4$, $R^5$, $R^6$ and $R^7$, respectively, in general formula (1) mentioned hereinabove. For the substituents for $R^{53}$, $R^{54}$, $R^{55}$, $R^{56}$ and $R^{57}$, referred to are those for $R^3$, $R^4$, $R^5$, $R^6$ and $R^7$ also mentioned hereinabove. $X^3$ in general formula (9) is a halogen atom, an imidazolyl group or a tetrazolyl group, but is preferably a halogen atom in view of the reactivity and the cost of the compound.

As in the above, in producing the phenylurethane compounds of the present invention, the amino compound to be reacted with the phenoxycarbonyl derivative is represented by any of general formula (4), (6) or (8) and has a long-chain alkyl group, and it uniformly disperses in the reaction system. Therefore, the novel, long-chain alkyl group-having phenylurethane compounds of the present invention are easy to produce. Asymmetric urea compounds and methods for producing them:

Next described are the asymmetric urea compounds and their production methods of the present invention.

The asymmetric urea compounds of the present invention have a long-chain alkyl group; and for producing them, a phenylurethane compound is reacted with an amino group having a long-chain alkyl group in the molecule.

The asymmetric urea compounds and their production methods of the present invention are described.

Asymmetric Urea Compounds

The asymmetric urea compounds of the present invention are represented by the following general formula (10):

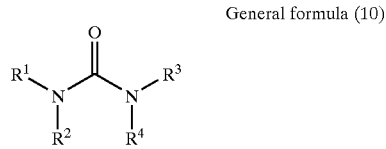

General formula (10)

wherein $R^1$ and $R^3$ each independently represent an alkyl group having from 8 to 30 carbon atoms in total, or an aralkyl group having from 8 to 30 carbon atoms in total.

The alkyl group having from 8 to 30 carbon atoms in total may be substituted or unsubstituted, including, for example, octyl, dodecyl, octadecyl, 3-dodecyloxypropyl, hexyloxycarbonylmethyl, octyloxycarbonylmethyl, dodecyloxycarbonylmethyl, decylaminocarbonylmethyl, dodecanesulfonylbenzyl and N-butylaminopropyl groups. Of those, preferred are alkyl groups each having from 8 to 20 carbon atoms in total.

The substituent for the optionally-substituted alkyl group includes, for example, an ester group, an ether group, a thioether group, a carbonyl derivative group, a cyano group, a carbamoyl group, a sulfamoyl group, and a urea group. Of those, preferred are an ester group, an ether group, and a carbamoyl group.

The aralkyl group having from 8 to 30 carbon atoms in total may be substituted or unsubstituted, including, for example, dodecylbenzyl, hexadecylbenzyl, dimethylbenzyl, octyloxybenzyl and octadecylaminocarbonylbenzyl groups. Of those, preferred are aralkyl groups each having from 8 to 20 carbon atoms in total. For the substituents for the optionally-substituted aralkyl group and for their preferred examples, referred to are those of the optionally-substituted alkyl group mentioned hereinabove for $R^1$.

In general formula (10), $R^2$ and $R^4$ each independently represent a hydrogen atom or an alkyl group.

The alkyl group for $R^2$ and $R^4$ may be substituted or unsubstituted, preferably having from 1 to 20 carbon atoms in total. Preferable examples thereof include methyl, ethyl, propyl, hexyl, octyl, dodecyl and octadecyl groups. Of those, more preferred are alkyl groups each having from 1 to 10 carbon atoms in total; even more preferred are alkyl groups each having from 1 to 8 carbon atoms in total; and especially preferred are methyl, ethyl and octyl groups. For the substituents for the optionally-substituted alkyl group and for their preferred examples, referred to are those mentioned hereinabove for $R^1$.

Preferably, $R^2$ and $R^4$ are hydrogen atoms.

In the asymmetric urea compounds of general formula (10), the combination of substituents $R^1$ and $R^2$ differs from the combination of substituents $R^3$ and $R^4$. Accordingly, the compounds have an asymmetric structure, and their solubility in organic solvents is high.

Of the asymmetric urea compounds of general formula (10), preferred are those of the following general formula (11):

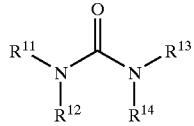

General formula (11)

wherein $R^{11}$ and $R^{13}$ each independently represent an unsubstituted alkyl group having from 8 to 30 carbon atoms in total, an unsubstituted aralkyl group having from 8 to 30 carbon atoms in total, an alkoxycarbonylmethyl group having from 8 to 30 carbon atoms in total, an aryloxycarbonylmethyl group having from 8 to 30 carbon atoms in total, an alkoxycarbonylethyl group having from 8 to 30 carbon atoms in total, an aryloxycarbonylethyl group having from 8 to 30 carbon atoms in total, or a carbamoylmethyl group.

The meaning of the unsubstituted alkyl group having from 8 to 30 carbon atoms in total for $R^{11}$ and $R^{13}$ is the same as that of the unsubstituted alkyl group for $R^1$ and $R^3$ mentioned hereinabove; and the meaning of the unsubstituted aralkyl group having from 8 to 30 carbon atoms in total for $R^{11}$ and $R^{13}$ is the same as that of the unsubstituted aralkyl group for $R^1$ and $R^3$ mentioned hereinabove.

In the alkoxycarbonylmethyl group having from 8 to 30 carbon atoms in total for $R^{11}$ and $R^{13}$, the alkoxy moiety may be substituted or unsubstituted, preferably having from 6 to 26 carbon atoms in total. The alkoxycarbonylmethyl group includes, for example, octyloxycarbonylmethyl, decyloxycarbonylmethyl, dodecyloxycarbonylmethyl and octadecyloxycarbonylmethyl groups.

Of those, more preferred are alkoxycarbonylmethyl groups in which the alkoxy moiety has from 6 to 22 carbon atoms in total; even more preferred are alkoxycarbonylmethyl groups in which the alkoxy moiety has from 8 to 18 carbon atoms; and especially preferred are octyloxycarbonylmethyl, decyloxycarbonylmethyl and dodecyloxycarbonylmethyl groups. For the substituents for the optionally-substituted groups and for their preferred examples, referred to are those mentioned hereinabove for the substituents for $R^1$.

In the aryloxycarbonylmethyl group having from 8 to 30 carbon atoms in total for $R^{11}$ and $R^{13}$, the aryl moiety may be substituted or unsubstituted. Preferably, in this, the aryloxy moiety has from 12 to 28 carbon atoms in total. The aryloxycarbonylmethyl group includes, for example, octyloxyphenoxycarbonylmethyl, decylsulfonylphenoxycarbonylmethyl, octylaminocarbonylphenoxycarbonylmethyl and dodecyloxycarbonylphenoxycarbonylmethyl groups.

Of those, more preferred are aryloxycarbonylmethyl groups in which the aryloxy moiety has from 12 to 22 carbon atoms in total; even more preferred are aryloxycarbonylmethyl groups in which the aryloxy moiety has from 14 to 22 carbon atoms; and especially preferred are octyloxyphenoxycarbonylmethyl and decanesulfonylphenoxycarbonylmethyl groups. For the substituents for the optionally-substituted groups and for their preferred examples, referred to are those mentioned hereinabove for the substituents for $R^1$.

In the alkoxycarbonylethyl group having from 8 to 30 carbon atoms in total for $R^{11}$ and $R^{13}$, the alkoxy moiety may be substituted or unsubstituted, preferably having from 5 to 25 carbon atoms in total. The alkoxycarbonylethyl group includes, for example, octyloxycarbonylethyl, decyloxycarbonylethyl, dodecyloxycarbonylethyl and octadecyloxycarbonylethyl groups.

Of those, more preferred are alkoxycarbonylethyl groups in which the alkoxy moiety has from 6 to 22 carbon atoms in total; even more preferred are alkoxycarbonylethyl groups in which the alkoxy moiety has from 7 to 18 carbon atoms; and especially preferred are octyloxycarbonylethyl and dodecyloxycarbonylethyl groups. For the substituents for the optionally-substituted groups and for their preferred examples, referred to are those mentioned hereinabove for the substituents for $R^1$.

In the aryloxycarbonylethyl group having from 8 to 30 carbon atoms in total for $R^{11}$ and $R^{13}$, the aryl moiety may be substituted or unsubstituted. Preferably, in this, the aryloxy moiety has from 12 to 25 carbon atoms in total. The aryloxycarbonylethyl group includes, for example, octyloxyphenoxycarbonylethyl, decanesulfonylphenoxycarbonylethyl, octylaminocarbonylphenoxycarbonylethyl and dodecyloxycarbonylphenoxycarbonylethyl groups.

Of those, more preferred are aryloxycarbonylethyl groups in which the aryloxy moiety has from 12 to 22 carbon atoms in total; even more preferred are aryloxycarbonylethyl groups in which the aryloxy moiety has from 14 to 22 carbon atoms; and especially preferred are octyloxyphenoxycarbonylethyl and decanesulfonylphenoxycarbonylethyl groups. For the substituents for the optionally-substituted groups and for their preferred examples, referred to are those mentioned hereinabove for the substituents for $R^1$.

In general formula (11), $R^{12}$ and $R^{14}$ each independently represent a hydrogen atom or an alkyl group, and the meaning of the alkyl group is the same as that of the alkyl group for $R^2$ and $R^4$ in general formula (10) mentioned hereinabove.

In the asymmetric urea compounds of general formula (11), the combination of substituents $R^{11}$ and $R^{12}$ differs from the combination of substituents $R^{13}$ and $R^{14}$. Accordingly, the compounds have an asymmetric structure, and their solubility in organic solvents is high.

Specific examples (Compounds (1') to (19')) of the asymmetric compounds of general formulae (10) and (11) are mentioned below, to which, however, the present invention is not limited.

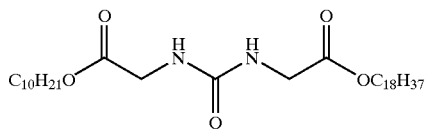

(1)'

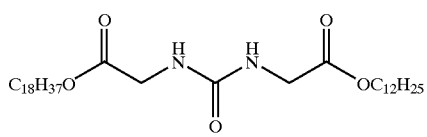

(2)'

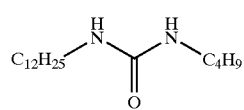

(3)'

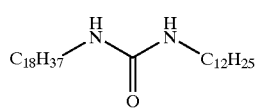

(4)'

-continued

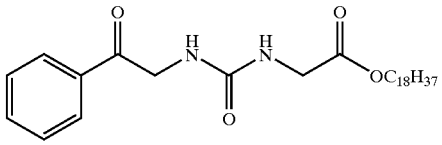

(5)'

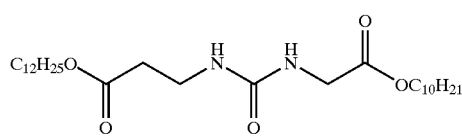

(6)'

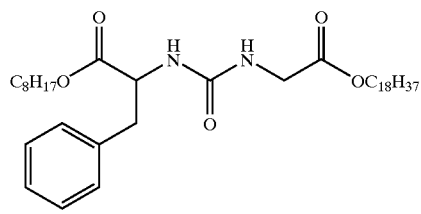

(7)'

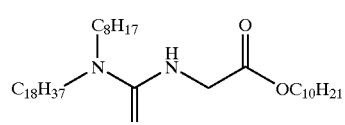

(8)'

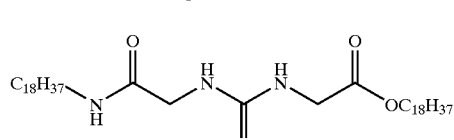

(9)'

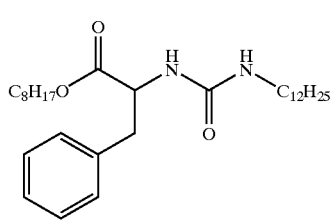

(10)'

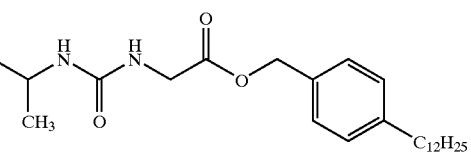

(11)'

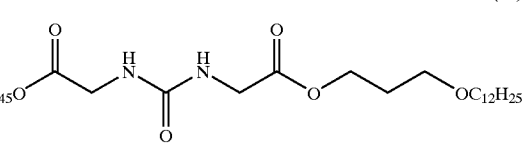

(12)'

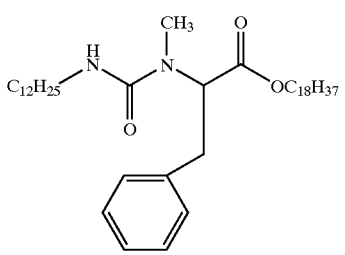

(13)'

Methods for Producing Asymmetric Urea Compounds

Next described are methods for producing the asymmetric urea compounds of the present invention.

The basic reaction mechanism for producing the asymmetric urea compounds of the present invention is shown by the following reaction formula I:

Reaction Formula I

General formula (12) + General formula (13) → Asymmetric Urea Compound

One method for producing the asymmetric urea compounds of general formula (10) of the present invention comprises reacting a phenylurethane compound of general formula (12) with an amino compound of general formula (13), in the presence of a base (preferably an organic base) in an organic solvent.

In this method, the phenylurethane compound of general formula (12) is the same as the phenylurethane compound of general formula (1) mentioned hereinabove. Therefore in the method for producing the asymmetric urea compounds of the present invention, used is the phenylurethane compound of general formula (1) for the starting material.

The reaction is effected in an organic solvent preferably under heat, in which, therefore, the product, asymmetric urea compound is dissolved or melted. Accordingly, the reaction efficiency is kept always high, and stirring the system is not retarded at all. The reaction to produce the asymmetric urea compound proceeds rapidly. Because of its asymmetric structure, the asymmetric urea compound of the present invention well dissolves in the solvent used.

The reaction I is effected in an organic solvent. The organic solvent includes, for example, N,N-dimethylformamide, N,N-dimethylacetamide, dimethylsulfoxide, N-methylpyrrolidone, acetonitrile, propionitrile, and tetrahydrofuran.

The reaction of the amino compound with the phenylurethane compound is effected in the presence of a base. For the base, preferred is an organic base. The reaction proceeds rapidly in the presence of a base, preferably an organic base. Preferred examples of the base (organic base) are trimethylamine, triethylamine, tributylamine, N,N-dimethylaniline, and 4-N,N-dimethylaminopyridine. The time in which the base is added to the reaction system may be determined in any desired manner, but is preferably before the starting material, the amino compound and/or the phenylurethane compound is added to the organic solvent. In other words, the base may be previously added to the organic solvent as so mentioned hereinabove.

The amount of the base (organic base) preferably is from 0.8 to 5.0 equivalents, more preferably from 0.9 to 2.0 equivalents to one equivalent of the phenylurethane compound.

The concentration of the phenylurethane compound to be reacted with the amino compound preferably is from 0.2 to 5.0 mols/liter, more preferably from 0.5 to 2.0 mols/liter.

If the concentration is smaller than 0.2 mols/liter, that is, if the amount of the phenylurethane compound is too small, the reaction will take a lot of time; but if larger than 5.0 mols/liter, that is, if the amount of the phenylurethane compound is too large, the reaction system will be difficult to stir.

The amount of the amino compound to be reacted with the phenylurethane compound preferably is from 0.8 to 5.0 equivalents, more preferably from 0.8 to 2.0 equivalents to one equivalent of the phenylurethane compound.

If the amount is smaller than 0.8 equivalents, the reaction will take a lot of time; but if larger than 5.0 equivalents, it is unfavorable in point of the production cost.

The reaction temperature preferably is from 50 to 110° C., more preferably from 65 to 90° C.

If the reaction temperature is lower than 50° C., the solubility of the amino compound in the solvent will be low and the reaction speed will be therefore lowered; but if higher than 110° C., it will cause side reactions to lower the yield of the product.

The starting materials in the reaction I, the phenylurethane compound of general formula (12) and the amino compound of general formula (13) are described.

In the reaction 1, $R^{21}$ and $R^{28}$ in general formulae (12) and (13) each are an alkyl group having from 8 to 30 carbon atoms in total, or an aralkyl group having from 8 to 30 carbon atoms in total, and their meanings are the same as those of $R^1$ and $R^3$ in general formula (10) mentioned hereinabove. For the substituents for $R^{21}$ and $R^{28}$, referred to are those for $R^1$ and $R^3$ also mentioned hereinabove. $R^{22}$ and $R^{29}$ each are a hydrogen atom or an alkyl group, and their meanings are the same as those of $R^2$ and $R^4$ in general formula (10) mentioned hereinabove. For the substituents for $R^{22}$ and $R^{29}$, referred to are those for $R^2$ and $R^4$ also mentioned hereinabove.

In the reaction I, $R^{23}$, $R^{24}$, $R^{25}$, $R^{26}$ and $R^{27}$ in general formula (12) each independently represent a hydrogen atom, a halogen atom, an alkoxy group, an aryloxy group, a carbonyl derivative group, or a nitro group.

The halogen atom for $R^{23}$ to $R^{27}$ includes, for example, fluorine, chlorine, bromine and iodine atoms, but is preferably a chlorine atom.

The alkoxy group for $R^{23}$ to $R^{27}$ may be substituted or unsubstituted, preferably having from 1 to 30 carbon atoms in total. Examples thereof include methoxy, ethoxy, butoxy, hexyloxy, octyloxy, dodecyloxy and octadecyloxy groups. Of those, more preferred are alkoxy groups each having from 1 to 20 carbon atoms in total; even more preferred are alkoxy groups each having from 1 to 8 carbon atoms in total; and especially preferred are methoxy, ethoxy and octyloxy groups.

The aryloxy group for $R^{23}$ to $R^{27}$ may be substituted or unsubstituted, preferably having from 1 to 30 carbon atoms in total. Examples thereof include phenoxy, methylphenoxy, dodecylphenoxy and dimethoxyphenoxy groups. Of those, more preferred are aryloxy groups each having from 1 to 20 carbon atoms in total; and even more preferred are aryloxy groups each having from 1 to 8 carbon atoms in total.

The carbonyl derivative group for $R^{23}$ to $R^{27}$ may be substituted or unsubstituted, including, for example, an alkylcarbonyl group having from 2 to 9 carbon atoms in total, and an arylcarbonyl group having from 7 to 15 carbon atoms in total.

The alkylcarbonyl group having from 2 to 9 carbon atoms in total includes, for example, methylcarbonyl, ethylcarbonyl, propylcarbonyl, butylcarbonyl, hexylcarbonyl and octylcarbonyl groups. Of those, preferred are alkylcarbonyl groups each having from 2 to 7 carbon atoms in total.

The arylcarbonyl group having from 7 to 15 carbon atoms in total includes, for example, phenylcarbonyl, methylphenylcarbonyl, ethylphenylcarbonyl, propylphenylcarbonyl, butylphenylcarbonyl, hexylphenylcarbonyl and octylphenylcarbonyl groups. Of those, preferred are arylcarbonyl groups each having from 7 to 12 carbon atoms in total.

For the substituents for the optionally-substituted alkoxy, aryloxy and carbonyl derivative groups for $R^{23}$ to $R^{27}$, and for their preferred examples, referred to are those mentioned hereinabove for the substituents for $R^1$.

For $R^{23}$ to $R^{27}$, preferred are a hydrogen atom and a nitro group.

The groups $R^{21}$, $R^{22}$, $R^{28}$ and $R^{29}$ in the product, asymmetric urea compound (this is the asymmetric urea compound of general formula (10)) in the reaction I correspond to those in general formulae (12) and (13).

Preferably, the phenylurethane compound of general formula (12) is prepared in a basic reaction mechanism of the following reaction formula II:

Reaction Formula II

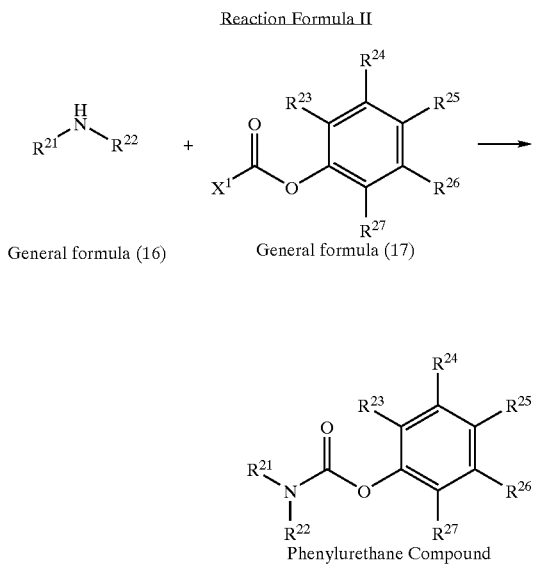

General formula (16)   General formula (17)

Phenylurethane Compound

As in the above, the phenylurethane compound of general formula (12) is prepared by reacting an amino compound of general formula (16) with a phenoxycarbonyl derivative of general formula (17) in the presence of a base in an aqueous solvent optionally containing an organic solvent that serves as an auxiliary solvent.

The reaction mechanism of the reaction II is the same as that of the method of reacting an amino compound of general formula (4) with a phenoxycarbonyl derivative of general formula (5) to give the phenylurethane compound of general formula (1) mentioned hereinabove.

In the reaction II, $R^{21}$ and $R^{22}$ in general formula (16), and $R^{23}$, $R^{24}$, $R^{25}$, $R^{26}$ and $R^{27}$ in general formula (17) correspond to $R^{21}$ and $R^{22}$ in general formula (12), and $R^{23}$, $R^{24}$, $R^{25}$, $R^{26}$ and $R^{27}$ in general formula (12), respectively. In general formula (17), $X^1$ represents a halogen atom, an imidazolyl group or a tetrazolyl group, but is preferably a halogen atom in view of the reactivity of the compound.

The reaction II is effected in a solvent, and the solvent is an aqueous solvent additionally containing an organic solvent that serves as an auxiliary solvent. The aqueous solvent includes, for example, water such as distilled water or ion-exchanged water, and a mixture of such water and a water-miscible solvent.

Adding an auxiliary solvent to the aqueous solvent makes it easy to stir the reaction system. The organic solvent that serves as the auxiliary solvent includes, for example, chloroform, ethyl acetate, tetrahydrofuran, acetone, methanol, ethanol, hexane, cyclohexane, toluene, acetonitrile and propionitrile. The ratio of the organic solvent to the aqueous solvent preferably is from 10 to 200% by weight, more preferably from 50 to 100% by weight of water in the aqueous solvent.

The reaction of the amino compound with the phenoxycarbonyl derivative is effected in the presence of a base, which promotes the reaction. Preferably, for example, the base is an alkali metal or alkaline earth metal salt.

The amount of the base preferably is from 0.9 to 4 equivalents, more preferably from 1 to 1.2 equivalents to one equivalent of the phenoxycarbonyl derivative.

The concentration of the amino compound to be reacted with the phenoxycarbonyl derivative preferably is from 0.5 to 4.0 mols/liter. The amount of the phenoxycarbonyl derivative preferably is from 0.8 to 2.0 equivalents to one equivalent of the amino compound.

The reaction temperature preferably is from 0 to 100° C., more preferably from 0 to 50° C., since the solvent, water must be kept liquid in the reaction system under atmospheric pressure.

For the reaction I of the phenylurethane compound of general formula (12) with the amino compound of general formula (13), preferred is a method of reacting a phenylurethane compound of the following general formula (14) with an amino compound of the following general formula (15). In this case, produced are asymmetric urea compounds of general formula (11) mentioned hereinabove.

General formula (14)

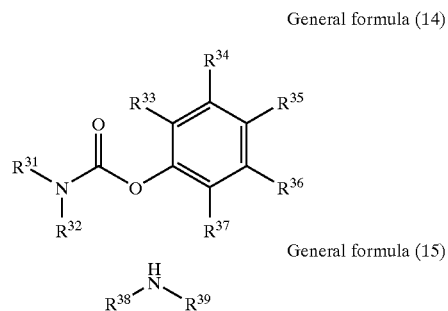

General formula (15)

In general formulae (14) and (15), $R^{31}$ and $R^{38}$ each independently represent an unsubstituted alkyl group having from 8 to 30 carbon atoms in total, an unsubstituted aralkyl group having from 8 to 30 carbon atoms in total, an alkoxycarbonylmethyl group having from 8 to 30 carbon atoms in total, an aryloxycarbonylmethyl group having from 8 to 30 carbon atoms in total, an alkoxycarbonylethyl group having from 8 to 30 carbon atoms in total, an aryloxycarbonylethyl group having from 8 to 30 carbon atoms in total, or a carbamoylmethyl group, and their meanings are the same as those of $R^{11}$ and $R^{13}$, respectively, in general formula (11) mentioned hereinabove. For the substituents for $R^{31}$ and $R^{38}$, referred to are those for $R^{11}$ and $R^{13}$ also mentioned hereinabove. $R^{32}$ and $R^{39}$ each independently represent a hydrogen atom or an alkyl group, and their meanings are the same as those of $R^2$ and $R^4$, respectively, in general formula (10) mentioned hereinabove. For the substituents for $R^{32}$ and $R^{39}$, referred to are those for $R^2$ and $R^4$, respectively, also mentioned hereinabove.

In general formula (14), $R^{33}$, $R^{34}$, $R^{35}$, $R^{36}$ and $R^{37}$ each independently represent a hydrogen atom, a halogen atom, an alkoxy group, an aryloxy group, a carbonyl derivative group, or a nitro group, and their meanings are the same as those of $R^{23}$, $R^{24}$, $R^{25}$, $R^{26}$ and $R^{27}$ in general formula (12) mentioned hereinabove. For the substituents for $R^{33}$, $R^{34}$, $R^{35}$, $R^{36}$ and $R^{37}$, referred to are those for $R^{23}$, $R^{24}$, $R^{25}$, $R^{26}$ and $R^{27}$ also mentioned hereinabove.

The phenylurethane compound of general formula (14) may be prepared according to the method of the reaction II mentioned above.

As in the above, in producing the asymmetric urea compounds of the present invention, the amino compound to be reacted with the phenylurethane compound is represented by any of general formula (13) or (15) and has a long-chain alkyl group, and it dissolves in the reaction system. The reaction of the amino compound with the phenylurethane compound proceeds rapidly, enabling efficient production of the asymmetric urea compounds. Therefore, the novel, long-chain alkyl group-having asymmetric urea compounds of the present invention are easy to produce.

Barbituric acid derivatives, and diazo thermal recording materials containing the derivatives:

Hereinunder described are the barbituric acid derivatives of the present invention that are produced from the asymmetric urea compounds mentioned above, and the diazo thermal recording material of the present invention that contains the barbituric acid derivative.

Barbituric Acid Derivatives

The barbituric acid derivatives of the present invention are represented by the following general formula (18):

General formula (18)

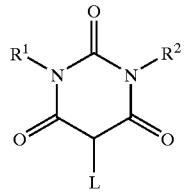

wherein $R^1$ and $R^2$ each independently represent an optionally-substituted alkyl group, or an optionally-substituted aralkyl group, and these differ from each other; L represents a hydrogen atom, or a substituent capable of leaving the compound when the compound is coupled with a diazo compound.

In the barbituric acid derivatives of general formula (18), $R^1$ differs from $R^2$. Accordingly, the barbituric acid derivatives have an asymmetric structure.

$R^1$ and $R^2$ each independently represent an optionally-substituted alkyl group, or an optionally-substituted aralkyl group. The alkyl group for these preferably has from 1 to 25 carbon atoms in total, more preferably from 5 to 25, even more preferably from 10 to 25 carbon atoms in total. The aralkyl group for these preferably has from 7 to 30 carbon atoms in total, more preferably from 10 to 30, even more preferably from 15 to 30 carbon atoms in total.

Preferred examples of the substituent for the substituted groups of $R^1$ and $R^2$ are an alkyl group having from 1 to 18 carbon atoms, an aryl group having from 6 to 20 carbon atoms, a hydroxyl group, an alkyloxy group having from 1 to 18 carbon atoms, an aryloxy group having from 6 to 20 carbon atoms, an alkylthio group having from 1 to 18 carbon atoms, an arylthio group having from 6 to 20 carbon atoms, an alkylcarbonyl group having from 2 to 25 carbon atoms, an arylcarbonyl group having from 7 to 35 carbon atoms, an alkoxycarbonyl group having from 2 to 25 carbon atoms, an acyloxy group having from 2 to 20 carbon atoms, a carbamoyl group having from 2 to 37 carbon atoms, an acylamino group having from 2 to 35 carbon atoms, an alkylsulfonyl group having from 2 to 20 carbon atoms, an arylsulfonyl group having from 7 to 20 carbon atoms, an alkylamino group having from 1 to 20 carbon atoms, an arylamino group having from 6 to 20 carbon atoms, a heterocyclic group, a halogen atom, a cyano group, and a nitro group. More preferably, the substituent is any of an alkyl group having from 1 to 18 carbon atoms, an alkyloxy group having from 1 to 18 carbon atoms, an alkylcarbonyl group having from 2 to 25 carbon atoms, an alkoxycarbonyl group having from 2 to 25 carbon atoms, and an acyloxy group having from 2 to 20 carbon atoms. The groups for the substituent may be optionally substituted.

L is a hydrogen atom, or a substituent capable of leaving the compound when the compound is coupled with a diazo compound (the substituent is hereinafter referred to as a leaving group). The compound (barbituric acid derivative) of general formula (18) may have one or more such leaving groups introduced thereinto.

The leaving group includes, for example, a halogen atom, an aromatic azo group, an alkyl, aryl or heterocyclic group that bonds to the coupling site of the compound via an oxygen, nitrogen, sulfur or carbon atom, an alkyl or arylsulfonyl group, an arylsulfinyl group, an alkyl, aryl or heterocyclic-carbonyl group, or a heterocyclic group that bonds to the coupling site of the compound via its nitrogen atom. Concretely, it includes, for example, a halogen atom, an alkoxy group, an aryloxy group, an acyloxy group, an alkyl or arylsulfonyloxy group, an acylamino group, an alkyl or arylsulfonamido group, an alkoxycarbonyloxy group, an aryloxycarbonyloxy group, an alkyl, aryl or heterocyclic-thio group, a carbamoylamino group, an arylsulfinyl group, an arylsulfonyl group, a 5-membered or 6-membered nitrogen-containing heterocyclic group, an imido group, and an arylazo group. The alkyl group and the heterocyclic group that may be in these leaving groups may be further substituted with, for example, any of an alkoxy group, an aryloxy group, a halogen atom, an alkoxycarbonyl group, and an alkylcarbonyloxy group.

The leaving group may also be an amino group, an ether group or a thioether group that bonds to the coupling site of the compound via a carbon atom. Concretely, the leaving group of the type includes dimethylaminomethyl, hydroxymethyl, ethoxymethyl, phenoxymethyl, methylthioxymethyl and phenylthioxymethyl groups.

In cases where the derivative has two or more leaving groups, they may be the same or different, and they may be further substituted with any of the substituents mentioned above.

If desired, the leaving group may form a ring, condensed with the coupler nucleus.

More precisely, the leaving group includes a halogen atom (fluorine, bromine, chlorine, iodine), an alkoxy group (e.g., ethoxy, dodecyloxy, methoxyethylcarbamoylmethoxy, carboxypropyloxy, methylsulfonylethoxy, ethoxycarbonylmethoxy), an aryloxy group (e.g., 4-methylphenoxy, 4-chlorophenoxy, 4-methoxyphenoxy, 4-carboxyphenoxy, 3-ethoxycarboxyphenoxy, 3-acetylaminophenoxy, 2-carboxyphenoxy), an acyloxy group (e.g., acetoxy, tetradecanoyloxy, benzoyloxy), an alkyl or arylsulfonyloxy group (e.g., methanesulfonyloxy, toluenesulfonyloxy), an acylamino group (e.g., dichloroacetylamino, heptafluorobutyrylamino), an alkyl or arylsulfonamido group (e.g., methanesulfonamido, trifluoromethanesulfonamido, p-toluenesulfonamido), an alkoxycarbonyloxy group (e.g., ethoxycarbonyloxy, benzyloxycarbonyloxy), an alkyl, aryl or heterocyclic-thio group (e.g., ethylthio, 2-carboxyethylthio, dodecylthio, 1-carboxydodecylthio, phenylthio, 2-butoxy-t-octylphenylthio, tetrazolylthio), an arylsulfonyl group (e.g., 2-butoxy-t-octylphenylsulfonyl), an arylsulfinyl group (e.g., 2-butoxy-t-octylphenylsulfinyl), a carbamoylamino group (e.g., N-methylcarbamoylamino, N-phenylcarbamoylamino), a 5-membered or 6-membered, nitrogen-containing heterocyclic group (e.g., imidazolyl, pyrazolyl, triazolyl, tetrazolyl, 1,2-dihydro-2-oxo-1-pyridyl), an imido group (e.g., succinimido, hydantoinyl), and an arylazo group (e.g., phenylazo, 4-methoxyphenylazo). These groups may be optionally substituted.

Hereinunder described is a method for producing the barbituric acid derivatives (barbituric acid compounds) of general formula (18).

For producing the barbituric acid compounds of general formula (18), 1 mol of an N,N'-disubstituted urea (in this, the two substituents differ from each other) is mixed with about 1.1 mols of malonic acid, about 3 mols of acetic anhydride and one liter of ethyl acetate, and refluxed for 3 hours. Next, a bad solvent such as methanol is added thereto, and the crystals formed are taken out through filtration to obtain the intended product, barbituric acid compound of general formula (18). In this method, the asymmetric urea compound of the present invention mentioned hereinabove may be used for the N,N'-disubstituted urea (in this, the two substituents differ from each other).

The leaving group L may be introduced into the barbituric compounds after the compounds have been produced according to the method mentioned above. For example, NCS (N-chloro-succinimide) may be used for introducing a chlorine atom into the compounds. Alternatively, a malonic acid having the leaving group L may be used in producing the barbituric acid compounds according to the method mentioned above.

Of the compounds of general formula (18), preferred are those of the following general formula (19):

General formula (19)

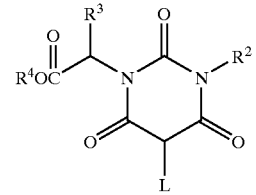

wherein $R^3$ represents a hydrogen atom, an optionally-substituted alkyl group, or an optionally-substituted aralkyl group; $R^4$ represents an optionally-substituted alkyl group or an optionally-substituted aralkyl group; and $R^3$ is independent of $R^4$.

The compounds of general formula (19) have an asymmetric structure, in which, therefore, the substituents bonding to the two nitrogen atoms differ from each other.

Of the compounds of general formula (18), more preferred are those of the following general formula (20):

General formula (20)

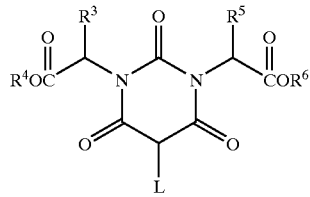

wherein $R^5$ represents a hydrogen atom, an optionally-substituted alkyl group, or an optionally-substituted aralkyl group; $R^6$ represents an optionally-substituted alkyl group or an optionally-substituted aralkyl group; and $R^5$ is independent of $R^6$.

The compounds of general formula (20) have an asymmetric structure, in which, therefore, the substituents bonding to the two nitrogen atoms differ from each other.

In cases where $R^3$, $R^4$, $R^5$ and $R^6$ in these compounds each independently represent an optionally-substituted alkyl group or an optionally-substituted aralkyl group, the optionally-substituted alkyl group preferably has from 1 to 25 carbon atoms in total, more preferably from 5 to 25, even more preferably from 10 to 25 carbon atoms in total. The optionally-substituted aralkyl group preferably has from 7 to 30 carbon atoms in total, more preferably from 10 to 30, even more preferably from 15 to 30 carbon atoms in total.

Preferred examples of the substituent for the substituted groups of $R^3$, $R^4$, $R^5$ and $R^6$ are an alkyl group having from 1 to 18 carbon atoms, an aryl group having from 6 to 20 carbon atoms, a hydroxyl group, an alkyloxy group having from 1 to 18 carbon atoms, an aryloxy group having from 6 to 20 carbon atoms, an alkylthio group having from 1 to 18 carbon atoms, an arylthio group having from 6 to 20 carbon atoms, an alkylcarbonyl group having from 2 to 25 carbon atoms, an arylcarbonyl group having from 7 to 35 carbon atoms, an alkoxycarbonyl group having from 2 to 25 carbon atoms, an acyloxy group having from 2 to 20 carbon atoms, a carbamoyl group having from 2 to 37 carbon atoms, an acylamino group having from 2 to 35 carbon atoms, an alkylsulfonyl group having from 2 to 20 carbon atoms, an arylsulfonyl group having from 7 to 20 carbon atoms, an alkylamino group having from 1 to 20 carbon atoms, an arylamino group having from 6 to 20 carbon atoms, a heterocyclic group, a halogen atom, a cyano group, and a nitro group. More preferably, the substituent is any of an alkyl group having from 1 to 18 carbon atoms, an alkyloxy group having from 1 to 18 carbon atoms, an alkylcarbonyl group having from 2 to 25 carbon atoms, an alkoxycarbonyl group having from 2 to 25 carbon atoms, and an acyloxy group having from 2 to 20 carbon atoms. The groups for the substituent may be optionally substituted.

Specific examples of barbituric acid derivatives of general formulae (18) to (20) are mentioned below, to which, however, the present invention is not limited.

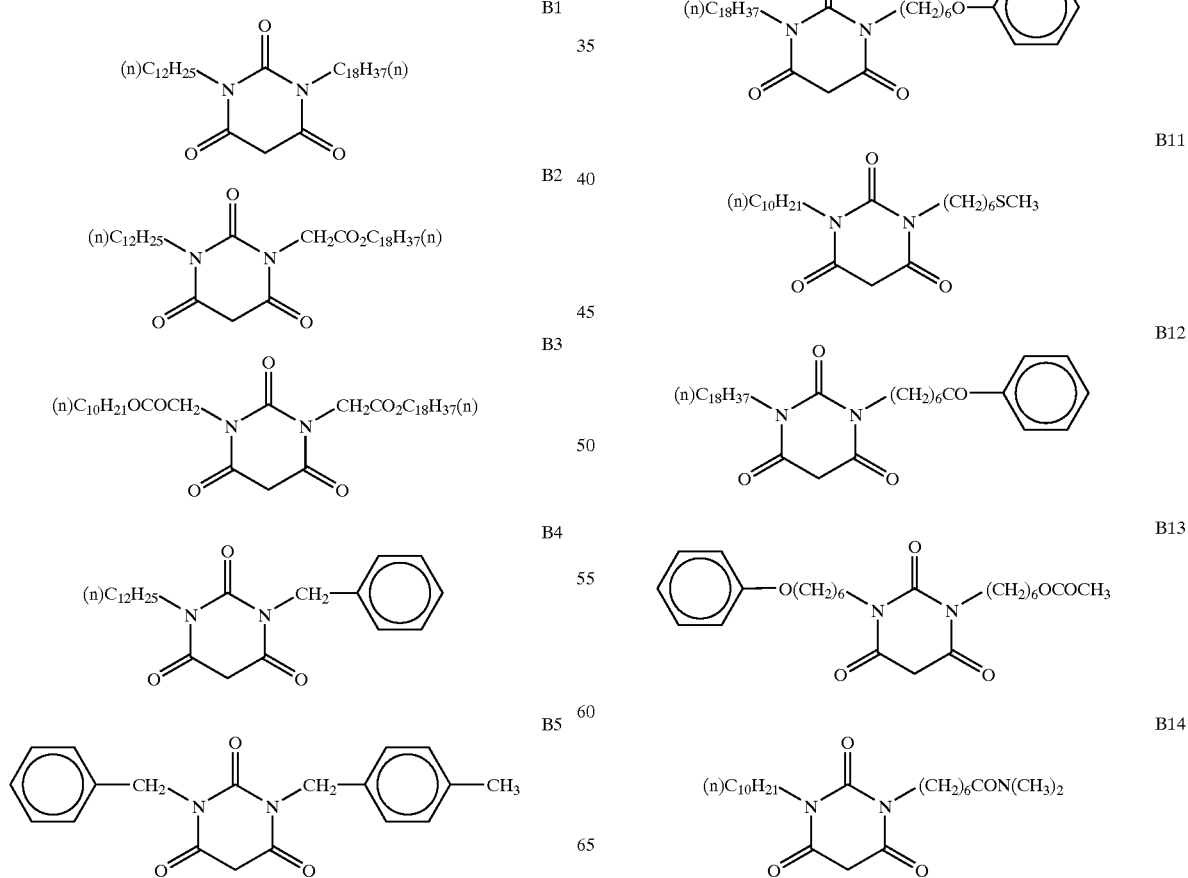

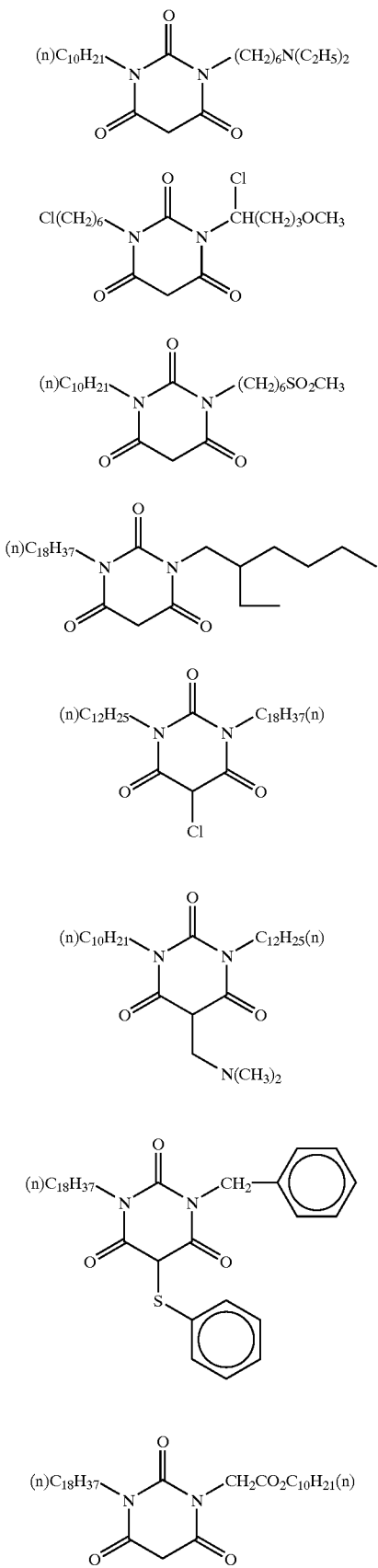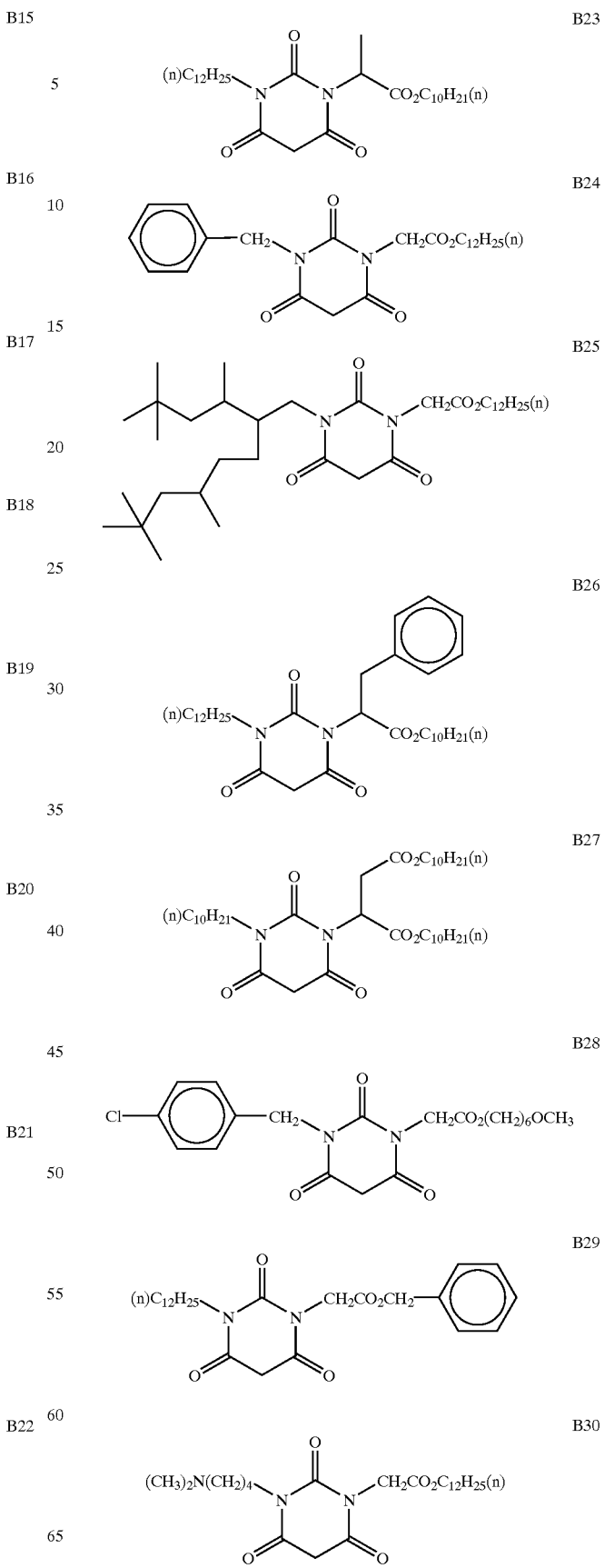

B31 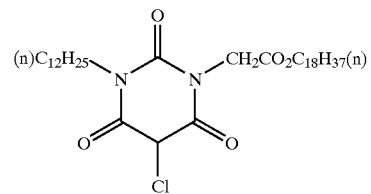
B32 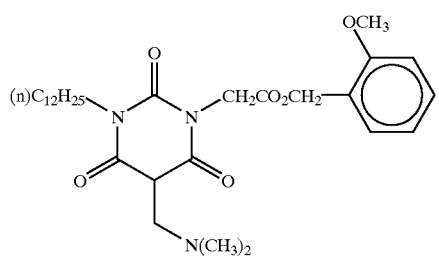
B33 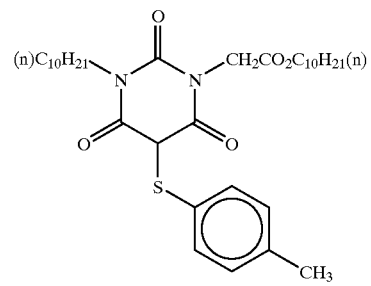
B34 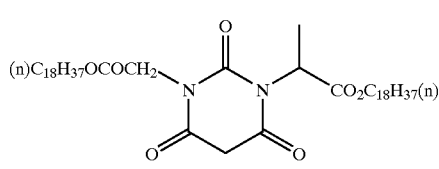
B35 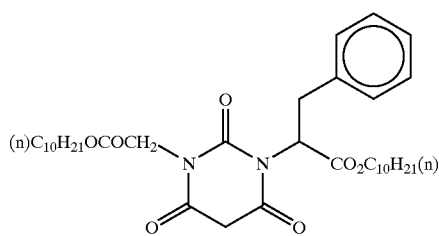
B36 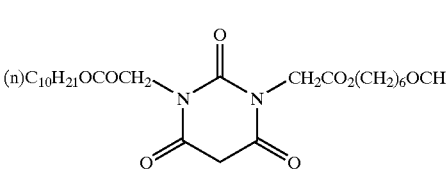
B37 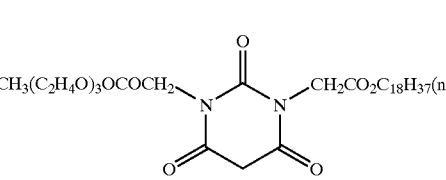
B38 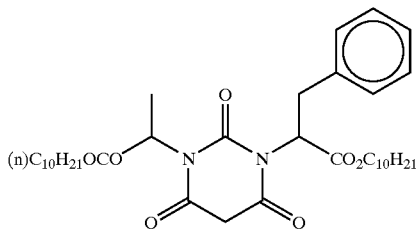
B39 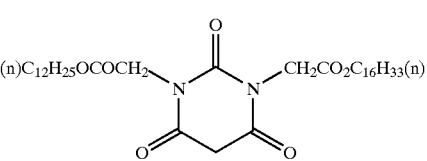
B40 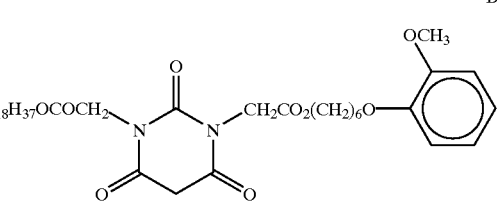
B41 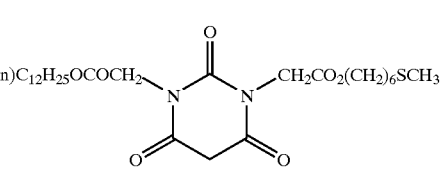
B42 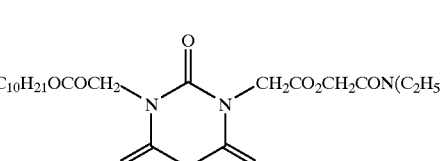
B43 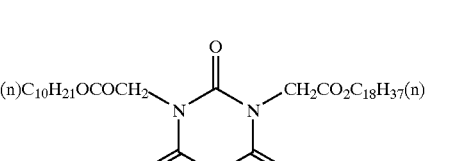
B44 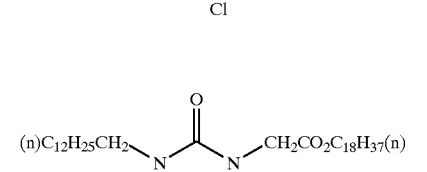

B45

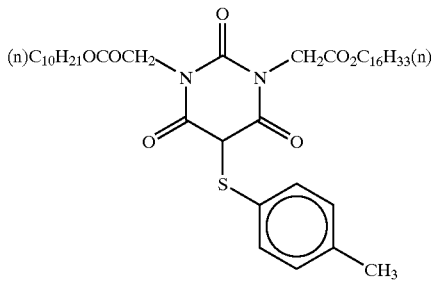

Diazo Thermal Recording Material

Next described is the diazo thermal recording material of the present invention.

The diazo thermal recording material of the present invention has, on a support, a thermal recording layer that contains a diazo compound, a coupling component and an organic base, in which the coupling component contains at least one compound of the following general formula (18):

General formula (18)

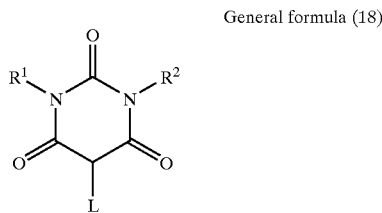

wherein $R^1$ and $R^2$ each independently represent an optionally-substituted alkyl group, or an optionally-substituted aralkyl group, and these differ from each other; L represents a hydrogen atom, or a substituent capable of leaving the compound when the compound is coupled with a diazo compound.

In the diazo thermal recording material having, on a support, a thermal recording layer that contains a diazo compound, a coupling component and an organic base, the compound (barbituric acid derivative) of general formula (18) can be used for the coupling component. For the coupling component in this, more preferred are compounds of the following general formula (19), and even more preferred are compounds of the following general formula (20).

General formula (19)

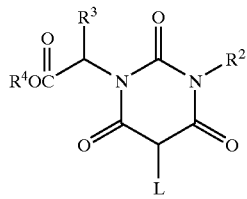

wherein $R^3$ represents a hydrogen atom, an optionally-substituted alkyl group, or an optionally-substituted aralkyl group; $R^4$ represents an optionally-substituted alkyl group or an optionally-substituted aralkyl group; and $R^3$ is independent of $R^4$.

General formula (20)

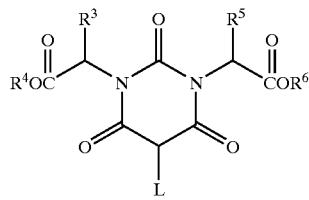

wherein $R^5$ represents a hydrogen atom, an optionally-substituted alkyl group, or an optionally-substituted aralkyl group; $R^6$ represents an optionally-substituted alkyl group or an optionally-substituted aralkyl group; and $R^5$ is independent of $R^6$.

In the thermal recording material of the present invention, the coupling component of general formulae (18) to (20) may be combined with any other known coupling component capable of coupling with a diazo compound in a basic atmosphere to form a dye, if desired for color control therein. Preferably, however, the coupling component of general formulae (18) to (20) in the recording material accounts for at least 50% by weight of all coupling components therein.

Known coupling components capable of being combined with the coupling component of general formulae (18) to (20) in the recording material are, for example, active methylene compounds in which the methylene group is adjacent to the carbonyl group therein, phenol derivatives, and naphthol derivatives.

Concretely, they include, for example, resorcinol, phloroglucinol, sodium 2,3-dihydroxynaphthalene-6-sulfonate, 1-hydroxy-2-naphthomorpholinopropylamide, 1,5-dihydroxynaphthalene, 2,3-dihydroxynaphthalene, 2,3-dihydroxy-6-sulfonaphthalene, 2-hydroxy-3-naphthomorpholinopropylamide, 2-hydroxy-3-naphthoctylamide, 2-hydroxy-3-naphthanilide, benzoylacetanilide, 1-phenyl-3-methyl-5-pyrazolone, 1-(2,4,6-trichlorophenyl)-3-anilino-5-pyrazolone, 2-{3-[α-(2,4-di-tert-amylphenoxy)-butanamido]benzamido}phenol, 2,4-bis-(benzoylacetamino)toluene, and 1,3-bis-(pivaloylacetaminomethyl)benzene.

In the diazo thermal recording material of the present invention, preferred for the diazo compound are those of the following general formula (21):

General formula (21)

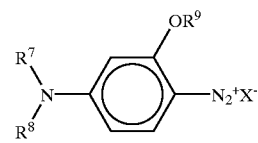

wherein $R^7$, $R^8$ and $R^9$ each independently represent an optionally-substituted alkyl group or an optionally-substituted aryl group; and X represents an anion.

The optionally-substituted alkyl group for $R^7$ and $R^8$ preferably has from 1 to 30, more preferably from 5 to 25 carbon atoms in total.

For example, it includes methyl, ethyl, n-propyl, isopropyl, n-butyl, isobutyl, n-pentyl, 2-pentyl, 3-pentyl, isopentyl, n-hexyl, n-octyl, 2-ethylhexyl, 3,5,5-trimethylhexyl, n-dodecyl, cyclohexyl, benzyl, allyl, 2-methoxyethyl, 2-ethoxyethyl, 2-phenoxyethyl, 2-(2,5-di-tert-amylphenoxy)ethyl, 2-benzoyloxyethyl, methoxycarbonylmethyl, methoxycarbonylethyl, butoxycarbonylethyl, 2-isopropyloxyethyl, 2-(4-methoxyphenoxy)ethyl, 3-(4-methoxyphenoxy)propane-2-yl, N,N-di(butyl)-carbamoylmethyl, N,N-di(hexyl)-carbamoylmethyl, N,N-di(ethyl)-carbamoylmethyl, piperidinocarbonylmethyl, 2-{N,N-di(butyl)-carbamoyl}ethyl, 1-{N,N-di(butyl)-carbamoyl}ethyl, and pyrrolidinocarbonylmethyl groups.

The optionally-substituted aryl group for $R^7$ and $R^8$ preferably has from 6 to 30, more preferably from 10 to 30 carbon atoms in total.

The anion for $X^-$ may be an inorganic or organic anion. Preferred examples of the inorganic anion are hexafluorophosphate, borohydrofluoride, chloride, hydrogensulfate, and sulfate ions. Preferred examples of the organic anion are polyfluoroalkylcarboxylate, polyfluoroalkylsulfonate, aromatic carboxylate, aromatic sulfonate, and tetraarylborate ions. Especially preferred are hexafluorophosphate and borohydrofluoride ions.

The optionally-substituted alkyl group for $R^9$ in general formula (21) preferably has from 1 to 30, more preferably from 5 to 25 carbon atoms in total.

For example, it includes methyl, ethyl, n-propyl, isopropyl, n-butyl, tert-butyl, sec-butyl, isobutyl, n-pentyl, 2-pentyl, 3-pentyl, isopentyl, n-hexyl, n-octyl, 2-ethylhexyl, 3,5,5-trimethylhexyl, n-dodecyl, cyclohexyl, benzyl, allyl, 2-chloroethyl, 2-methoxyethyl, 2-ethoxyethyl, 2-phenoxyethyl, 2-(2,5-di-tert-amylphenoxy)ethyl, 2-benzoyloxyethyl, methoxycarbonylmethyl, methoxycarbonylethyl, butoxycarbonylethyl, and 2-isopropyloxyethyl groups.

The optionally-substituted aryl group for $R^9$ preferably has from 6 to 30, more preferably from 10 to 30 carbon atoms in total.

For example, it includes phenyl, 4-methylphenyl, 3-methylphenyl, 2-methylphenyl, 4-chlorophenyl, and 2-chlorophenyl groups.

Specific examples (A-1 to A-10) of the diazo compounds of general formula (21) are mentioned below, to which, however, the present invention is not limited.

A-1

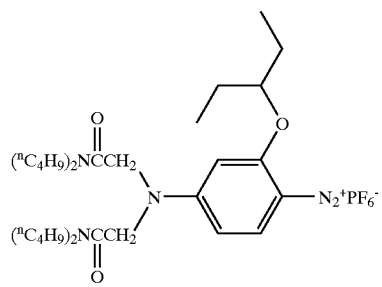

A-2

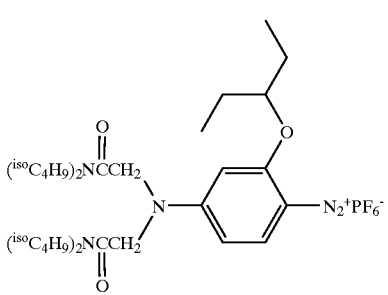

A-3

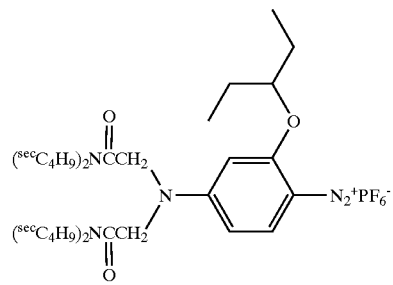

A-4

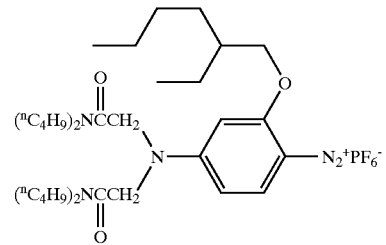

A-5

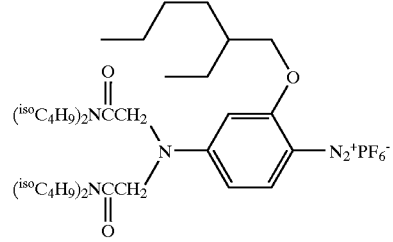

A-6

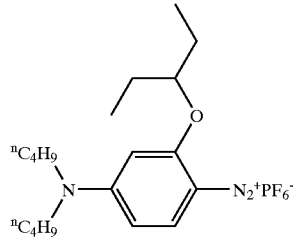

A-7

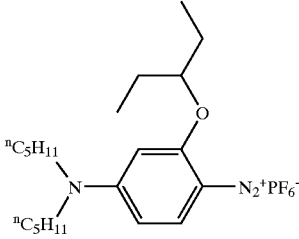

A-8

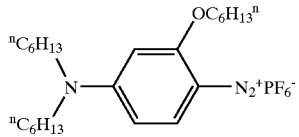

-continued

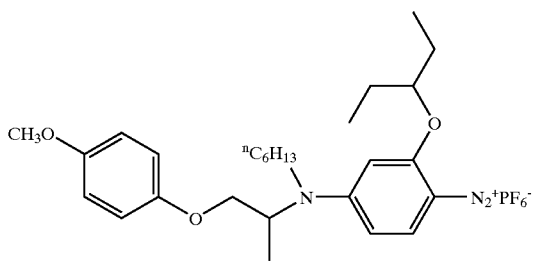

A-9

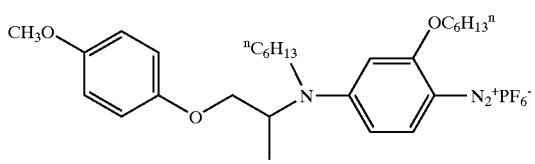

A-10

One or more of the diazo compounds of general formula (21) may be used herein, either singly or as combined. If desired, the diazo compound of general formula (21) may be combined with any other known diazo compound for color control in the recording material. Preferably, however, the diazo compound (diazonium salt) of general formula (21) in the recording material accounts for at least 50% by weight of all diazo compounds therein.

Preferred examples of the additional diazo compounds that may be in the recording material are 4-diazo-1-dimethylaminobenzene, 4-diazo-2-butoxy-5-chloro-1-dimethylaminobenzene, 4-diazo-1-methylbenzylaminobenzene, 4-diazo-1-ethylhydroxyethylaminobenzene, 4-diazo-1-diethylamino-3-methoxybenzene, 4-diazo-1-morpholinobenzene, 4-diazo-1-morpholino-2,5-dibutoxybenzene, 4-diazo-1-toluylmercapto-2,5-diethoxybenzene, 4-diazo-1-piperazino-2-methoxy-5-chlorobenzene, 4-diazo-1-(N,N-dioctylaminocarbonyl)benzene, 4-diazo-1-(4-tert-octylphenoxy)benzene, 4-diazo-1-(2-ethylhexanoylpiperidino)-2,5-dibutoxybenzene, 4-diazo-1-[α-(2,4-di-tert-amylphenoxy)butyrylpiperidino]benzene, 4-diazo-1-(4-methoxy)phenylthio-2,5-diethoxybenzene, 4-diazo-1-(4-methoxy)benzamido-2,5-diethoxybenzene, and 4-diazo-1-pyrrolidino-2-methoxybenzene.

In the diazo thermal recording material of the present invention, the diazo compound is preferably encapsulated in microcapsules for enhancing the raw-stock storability of the material before use, as will be mentioned in detail hereinunder. For its encapsulation, the diazo compound is dissolved in a suitable solvent. Therefore, it is desirable that the diazo compound is soluble in solvents in some degree but is hardly soluble in water. Concretely, it is desirable that the solubility of the diazo compound in the organic solvent used is at least 5% and the solubility thereof in water is at most 1%.

Preferably, the amount of the diazo compound to be in the thermal recording layer of the diazo thermal recording material of the present invention is from 0.02 to 3 g/m², more preferably from 0.1 to 2 g/m² for ensuring good color density.

As so mentioned hereinabove, the diazo compound in the diazo thermal recording material of the present invention is preferably encapsulated in microcapsules for enhancing the raw-stock storability of the material before use.

Microcapsules of the diazo compound may be prepared, for example, as follows: The diazo compound is dissolved in a non-aqueous solvent of which the boiling point at atmospheric pressure is from 40 to 95° C., along with compounds of the same type or different types capable of reacting with each other to form a polymer substance, and the resulting solution is emulsified and dispersed in a hydrophilic protective colloid in a reactor. While the reactor is degassed, the emulsion therein is heated. In that condition, the solvent is removed from the emulsion and the wall-forming substances are moved toward the oil drops and polymerized around them in a mode of addition polymerization or polycondensation to thereby form a polymer wall film that encapsulates every oil drop.

Preferably, the microcapsules to be in the diazo thermal recording material of the present invention does not substantially contain a solvent, as will be described hereinunder, for prolonging the shelf life of the recording material. Also preferably, the polymer substance to form the microcapsule wall is at least one selected from polyurethanes and polyureas.

One method of forming the diazonium salt-containing microcapsules (polyurea-polyurethane walls) to be in the diazo thermal recording material of the present invention is described below.

First, a diazonium salt is dissolved in a hydrophobic organic solvent that forms a core of each microcapsule. In this step, the organic solvent is preferably at least one selected from halogenohydrocarbons, carboxylates, phosphates, ketones and ethers. To the core solvent, added is a wall material, polyisocyanate (oily phase).

On the other hand, an aqueous solution of a water-soluble polymer such as polyvinyl alcohol or gelatin is prepared to be an aqueous phase. Then, the oily phase is put into the aqueous phase and emulsified and dispersed by the use of a homogenizer or the like. In this step, the water-soluble polymer serves as a stabilizer for the emulsion. For further stabilizing the emulsion, a surfactant may be added to at least one of the oily phase or the aqueous phase.

The amount of the polyisocyanate to be used herein is so defined that the mean particle size of the microcapsules formed could are from 0.3 to 12 μm and the wall thickness thereof could are from 0.01 to 0.3 μm. The particle size of the dispersed microcapsules generally is from 0.2 to 10 μm or so. In the emulsified dispersion, the polyisocyanate polymerizes in the interface between the oily phase and the aqueous phase to form a polyurea wall.

If desired, a polyol may be added to the aqueous phase, and it will react with the polyisocyanate to form a polyurethane wall. In the reaction to form the microcapsule walls, it is desirable to elevate the reaction temperature or to add a suitable polymerization catalyst to the system for accelerating the reaction speed. Polyisocyanates, polyols, reaction catalysts, and also polyamines that partly assist microcapsule wall formation are described in detail in some references (e.g., Keiji Iwata's *Polyurethane Handbook*, Nikkan Kogyo Shinbun-sha, 1987).

The hydrophobic organic solvent that dissolves diazonium salts and forms microcapsule cores preferably has a boiling point of from 100 to 300° C. Concretely, it includes alkylnaphthalenes, alkyldiphenylethanes, alkyldiphenylmethanes, alkylbiphenyls, chloroparaffins, tricresyl phosphate, maleates, adipates, sulfates, and sulfonates. Two or more of these may be used herein, as combined.

In cases where the diazonium salt to be encapsulated is poorly soluble in these solvents, a low-boiling-point solvent in which the solubility of the diazonium salt is high may be used along with the hydrophobic organic solvent. The lowboiling-point solvent includes, for example, ethyl acetate, butyl acetate, methylene chloride, tetrahydrofuran, and acetone. The low-boiling-point solvent, if used alone for microcapsule cores, evaporates during the process of encapsulation, and coreless microcapsules are formed in which the capsule wall is integrated with the diazo compound therein.

For the polyisocyanate compound for the microcapsule wall material, preferred are those having a trifunctional or more polyfunctional isocyanate group, but such polyisocyanate compounds may be combined with difunctional isocyanate compounds. Concretely, they include, for example, dimers or trimers (biurets or isocyanurates) consisting essentially of diisocyanates such as xylylene diisocyanate and its hydrogenates, hexamethylene diisocyanate, tolylene diisocyanate and its hydrogenates, isophorone diisocyanate; as well as polyfunctional adducts with polyols such as trimethylolpropane, and formalin condensates with benzene isocyanate.

If desired, an additional, microcapsule wall-forming ingredient selected from polyols or polyamines may be added to the core-forming, hydrophobic solvent or to the dispersion medium, water-soluble polymer solution. Examples of the polyols and polyamines are propylene glycol, glycerin, trimethylolpropane, triethanolamine, sorbitol, and hexamethylenediamine. When a polyol is added to the reaction system, then a polyurethane wall is formed.

Regarding the solubility in water of the water-soluble polymer to form the aqueous solution in which the thus-formed oily phase for microcapsules is dispersed, it is desirable that the solubility of the polymer in water at a temperature at which the oily phase is emulsified is at least 5%. Examples of the water-soluble polymer of the type are polyvinyl alcohol and its modified derivatives, polyacrylamide and its derivatives, ethylene-vinyl acetate copolymers, styrene-maleic anhydride copolymers, ethylene-maleic anhydride copolymers, isobutylene-maleic anhydride copolymers, polyvinylpyrrolidone, ethylene-acrylic acid copolymers, vinyl acetate-acrylic acid copolymers, carboxymethyl cellulose, methyl cellulose, casein, gelatin, starch derivatives, gum arabic, and sodium alginate.

Preferably, these water-soluble polymers have no or little reactivity with isocyanate compounds. Therefore, for example, gelatin and others having a reactive amino group in the molecular chain must be pre-modified so as to make them inactive. In cases where a surfactant is added to the emulsion for microcapsule formation, its amount falls preferably from 0.1% to 5%, more preferably from 0.5% to 2% by weight of the oily phase to form the emulsion.

Emulsifying the components may be effected in any known emulsifying device, such as homogenizer, Manton Gaulin, ultrasonic disperser or Keddy mill. After having been thus emulsified, the resulting emulsion is kept heated at 30 to 70° C. for promoting its capsule wall formation. During the reaction, cohesion of microcapsules being formed must be prevented. For this, water will be added to the reaction system to lower the probability of collision of microcapsules with each other; or the system will be fully stirred.

As the case may be, an additional dispersant may be added to the reaction system to prevent cohesion of microcapsules. With the progress of polymerization, carbon dioxide is formed. The time at which the formation of carbon dioxide is terminated will be nearly the end point of the microcapsule wall formation. In general, the intended, diazonium salt-containing microcapsules can be formed within a few hours after the start of the reaction.

The diazo thermal recording material of the present invention contains an organic base which acts to promote the coupling reaction of the diazo compound and the coupler in the material.

One or more different types of organic bases are used therein either singly or as combined. The organic base includes, for example, nitrogen-containing compounds such as tertiary amines, piperidines, piperazines, amidines, formamidines, pyridines, guanidines, and morpholines.

Of those, especially preferred for use herein are piperazines such as N,N'-bis(3-phenoxy-2-hydroxypropyl) piperazine, N,N'-bis[3-(p-methylphenoxy)-2-hydroxypropyl]piperazine, N,N'-bis[3-(p-methoxyphenoxy)-2-hydroxypropyl]piperazine, N,N'-bis(3-phenylthio-2-hydroxypropyl)piperazine, N,N'-bis[3-(β-naphthoxy)-2-hydroxypropyl]piperazine, N-3-(β-naphthoxy)-2-hydroxypropyl-N'-methylpiperazine, 1,4-bis{[3-(N-methylpiperazino)-2-hydroxy]propyloxy}benzene; morpholines such as N-[3-(β-naphthoxy)-2-hydroxy] propylmorpholine, 1,4-bis[(3-morpholino-2-hydroxy) propyloxy]benzene, 1,3-bis[(3-morpholino-2-hydroxy) propyloxy]benzene; piperidines such as N-(3-phenoxy-2-hydroxypropyl)piperidine, N-dodecylpiperidine; and guanidines such as triphenylguanidine, tricyclohexylguanidine, dicyclohexylphenylguanidine.

In the diazo thermal recording material of the present invention, it is desirable that the amount of the coupling component and that of the basic substance each are from 0.1 to 30 parts by weight relative to 1 mol of the diazo compound therein. In addition to the organic base mentioned above, the recording material of the present invention may further contain a color-forming reaction promoter for promoting the color-forming reaction in the material. The color-forming reaction promoter has the property of increasing the color density of the material recorded under heat or lowering the lowermost color-forming temperature of the material. Concretely, it acts to lower the melting point of the coupler, the basic substance or the diazo compound in the recording material of the present invention, or acts to lower the softening point of the walls of the microcapsules therein, thereby facilitating the reaction of the diazo compound, the basic compound and the coupler in the material.

The color-forming reaction promoter usable in the diazo thermal recording material of the present invention includes, for example, phenol derivatives, naphthol derivatives, alkoxy-substituted benzenes, alkoxy-substituted naphthalenes, hydroxy compounds, amide compounds and sulfonamide compounds; and it may be in the thermal recording layer of the material to ensure rapid and complete color formation in the layer at low energy. It is believed that these compounds will act to lower the melting point of the coupling component and the basic substance in the recording material, or to increase the heat permeability though the microcapsule walls therein, and will therefore ensure increased color density of the recorded material.

The color-forming reaction promoter encompasses thermal fusing substances which are solid at room temperature but melt under heat and which have a melting point falling from 50° C. to 150° C. The substances dissolve the diazo compound, the coupling component or the basic substance in the recording material of the present invention. Concretely, for example, they are carbonamides, N-substituted carbonamides, ketone compounds, urea compounds, and esters. The recording material of the present invention preferably contains a known antioxidant such as those mentioned below, for further improving the fastness to light and heat of the color images recorded thereon and for preventing as much as possible the non-image area of the material from being yellowed by light after image fixation thereon.

Antioxidants usable for the purpose are described in, for example, European patent publication Nos. 223,739, 309, 401, 309,402, 310,551, 310,552, and 459,416; German patent publication No.3,435,443; JP-A Nos. 54-48535, 62-262047, 63-113536, 63-163351,2-262654, 2-71262, 3-121449, 5-61166, and 5-119449; and U.S. Pat. Nos. 4,814, 262 and 4,980,275.

In addition, other various additives known in the art of thermal recording materials and pressure-sensitive recording materials are also effective in the present invention. Examples of the additives are described in, for example, JP-A Nos. 60-107384, 60-107383, 60-125470, 60-125471, 60-125472, 60-287485, 60-287486, 60-287487, 60-287488, 61-160287, 61-185483, 61-211079, 62-146678, 62-146680, 62-146679, 62-282885, 63-051174, 63-89877, 63-88380, 63-088381, 63-203372, 63-224989, 63-251282, 63-267594, 63-182484, 1-239282, 4-291685, 4-291684, 5-188687, 5-188686, 5-110490, and 5-170361; and JP-B Nos.48-043294 and 48-033212.

Concretely mentioned for them are 6-ethoxy-1-phenyl-2, 2,4-trimethyl-1,2-dihydroquinoline, 6-ethoxy-1-octyl-2,2,4-trimethyl-1,2-dihydroquinoline, 6-ethoxy-1-phenyl-2,2,4-trimethyl-1,2,3,4-tetrahydroquinoline, 6-ethoxy-1-octyl-2,2, 4-trimethyl-1,2,3,4-tetrahydroquinoline, nickel cyclohexanoate, 2,2-bis(4-hydroxyphenyl)propane, 1,1-bis-4-hydroxyphenyl-2-ethylhexane, 2-methyl-4-methoxy-diphenylamine, 1-methyl-2-phenylindole.

Preferably, the amount of the antioxidant that may be in the recording material of the present invention is from 0.05 to 100 parts by weight, more preferably from 0.2 to 30 parts by weight, relative to 1 part by weight of the diazo compound therein. The known antioxidant may be in microcapsules along with the diazo compound therein, or may form a solid dispersion along with the coupling component, the basic substance and the other color-forming reaction promoter therein, or may form an emulsion along with a suitable emulsification promoter therein, or may even be in any form of their combinations. Not only one but also two or more different types of the antioxidants may be used herein either singly or as combined. If desired, the antioxidant may be in the protective layer optionally formed on the thermal recording layer of the material of the present invention.

The antioxidant may not be in one and the same layer of the material. In cases where two or more different types of antioxidants are combined for use herein, they may be grouped into anilines, alkoxybenzenes, hindered phenols, hindered amines, hydroquinone derivatives, phosphorus compounds and sulfur compounds with respect to their structures, and two or more of them that differ from each other in point of their structures may be combined; or two or more of them of the same type may be combined.

In cases where L in general formula (18) that represents the coupling component to be in the recording material of the present invention is not a hydrogen atom but a substituent capable of leaving the compound when the compound is coupled with a diazonium salt compound, a reducing agent or a hydrogen donor is preferably combined with the coupling component of the type. Any known reducing agent or hydrogen donor may be used, but preferred are the compounds mentioned below.

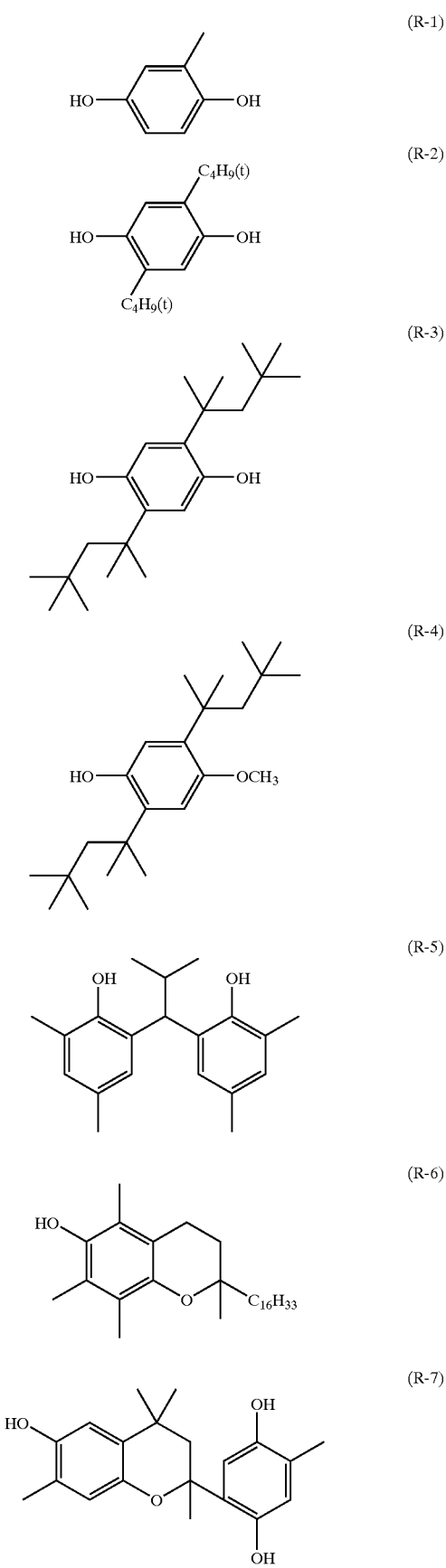

-continued

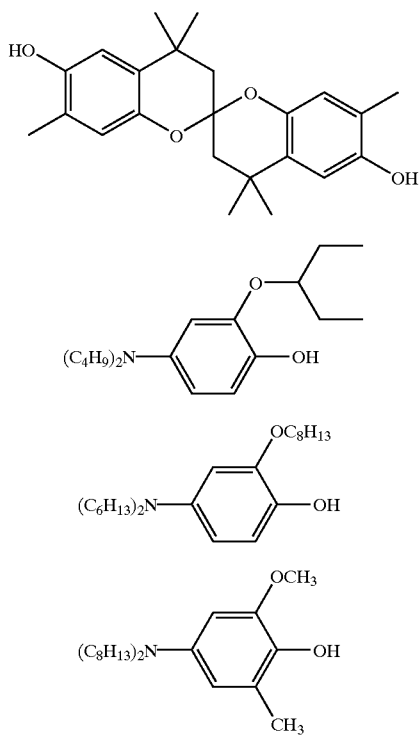

(R-8)

(R-9)

(R-10)

(R-11)

Along with the basic substance, the color-forming reaction promoter and other components that constitute the recording material of the present invention, the coupling component may be dispersed in solid in a water-soluble polymer by the use of a sand mill or the like. Preferably, however, the coupling component is emulsified along with a suitable emulsifier to form an emulsion. The water-soluble polymer to be used for solid dispersion may be the same as that used in microcapsule formation (see, for example, JP-A No. 59-190886). In this case, the amount of the coupling component, the basic substance and the color-forming reaction promoter each are from 5 to 40% by weight of the water-soluble polymer. The particle size of the dispersed or emulsified particles is preferably at most 10 μm.

The diazo thermal recording material of the present invention may further contain a free radical generator generally used in photopolymerizable compositions (this is a compound that generates a free radical through exposure to light), for the purpose of preventing the background area of the image-fixed material from being yellowed. The free radical generator includes, for example, aromatic ketones, quinones, benzoins, benzoin ethers, azo compounds, organic disulfides, and acyloxime esters. The amount of the free radical generator that may be added to the material preferably is from 0.01 to 5 parts by weight relative to 1 part by weight of the diazo compound in the material.

Also for preventing its yellowing, the material may contain an ethylenic unsaturated bond-having polymerizable compound (hereinafter referred to as vinyl monomer). The vinyl monomer is a compound having at least one ethylenic unsaturated bond (e.g., vinyl group, vinylidene group) in the chemical structure, and may be in any chemical form of monomers or prepolymers. Examples thereof include unsaturated carboxylic acids and their salts, esters of unsaturated carboxylic acids with aliphatic polyalcohols, and amides of unsaturated carboxylic acids with aliphatic polyamines.

The amount of the vinyl monomer that may be in the material may are from 0.2 to 20 parts by weight relative to 1 part by weight of the diazo compound therein. The free radical generator and the vinyl monomer may be in microcapsules along with the diazo compound therein. In addition to the components mentioned above, the diazo thermal recording material of the present invention may further contain any of citric acid, tartaric acid, oxalic acid, boric acid, phosphoric acid or pyrophosphoric acid serving as an acid stabilizer.

One preferred method for fabricating the diazo thermal recording material of the present invention is as follows: A coating liquid that contains a diazo compound in microcapsules, a coupling component, an organic base and other additives is prepared, and this is applied onto a support of, for example, paper or synthetic resin film in a mode of bar coating, blade coating, air-knife coating, gravure coating, roll coating, spraying, dipping, curtain coating or the like, and dried to form thereon a thermal recording layer having a solid content of from 2.5 to 30 $g/m^2$.

In the diazo thermal recording material of the present invention, the microcapsules, the coupling component and the base may be in one and the same layer, but may be in different layers that form a laminate structure. If desired, an interlayer may be formed on the support, as in JP-A No. 61-54980, and a thermal recording layer comprising the constituent components may be formed thereon.

For the support of the diazo thermal recording material of the present invention, usable is any and every paper support generally used in ordinary pressure-sensitive copying paper or thermal copying paper or in dry or wet diazo copying paper. In addition, also usable are neutral paper sized with a neutral sizing agent such as alkylketene dimer and having a pH of from 5 to 9 (as in JP-A No.55-14281); paper that satisfies the relationship between the Stoeckigt sizing degree and the metric unit weight indicated in JP-A No. 57-116687 and has a Beck smoothness of at least 90 seconds; paper having an optical surface roughness of at most 8 μm and a thickness of from 30 to 150 μ, as in JP-A No. 58-136492; paper having a density of at most 0.9 $g/cm^3$ and an optical contact degree of at least 15%, as in JP-A No. 58-6909 1; paper made of pulp having been beaten to a Canadian Standard Freeness (JIS P8121) of at least 400 cc, and specifically processed so as to prevent coating liquid from penetrating therethrough, as in JP-A No. 58-69097; paper modified from Yankee-made base paper—its glossy surface is coated with recording layer and the color density and the resolution of the coated paper are improved, as in JP-A No. 58-65695; and paper processed by corona discharging so as to have improved coatability, as in JP-A No. 59-35985.

The synthetic resin film for the support of the recording material of the present invention may be selected from any known ones of good dimensional stability not deforming under heat in development. The film of the type includes, for example, polyester films such as polyethylene terephthalate or polybutylene terephthalate films; cellulose derivative films such as cellulose triacetate films; as well as polystyrene films, polypropylene films and other polyolefin films such as polyethylene films. These may be used alone or as combined into laminates. The thickness of the support may are from 20 to 200 μm.

Preferably, a protective layer is formed on the thermal recording layer of the diazo thermal recording material of the present invention. This is for preventing the recording layer from sticking to the thermal head used in image formation on the material or for preventing the thermal head from being soiled by the material. This is also for making the recording material resistant to water. The recording layer may comprise, as the essential ingredient, polyvinyl alcohol or the like and may contain pigment or lubricant.

When the recording surface of the diazo thermal recording material of the present invention is heated with a thermal head or the like, the polyurea or polyurethane capsule walls in the material are softened, and as a result, the coupler and the basic compound that exist outside the microcapsules in the material penetrate into the microcapsules to form a color. After thus recorded, the material is exposed to light capable of being absorbed by the diazo compound therein, and the diazo compound is thus decomposed and loses its activity with the coupler in the material. Through the exposure, the recorded image is fixed in the material.

For the light source for image fixation, usable are various fluorescent lamps, xenon lamps and mercury lamps. For efficient optical fixation in the image-recorded material, it is desirable that the emission spectrum of the light source almost corresponds to the absorption spectrum of the diazo compound in the recording material. For image formation thereon, the thermal recording material of the present invention may be processed as follows: The material is exposed to light via an original image, then the diazo compound not in the image area of the exposed material is decomposed to form a latent image, and the material is heated to develop the latent image into a visible image.

EXAMPLES

The present invention is described in more detail with reference to the following Examples, which, however, are not intended to restrict the scope of the present invention.
Production of Phenylurethane Compounds In the method of phenylurethane formation mentioned below, the reactants were stirred and reacted in a four-neck flask equipped with a mechanical stirrer, a thermometer and two dropping funnels, in a water bath.

Example 1

194 g of decyl 2-aminoacetate methanesulfonate was added to 0.5 liters of water, and stirred. An aqueous solution of 41 g of sodium acetate in 0.3 liters of water, and 78.3 g of phenyl chloroformate were separately put into dropping funnels, through which they were simultaneously dripped into it with taking care that the inner temperature do not exceed 50° C. These were reacted for 10 minutes, and then 41 g of sodium acetate was added thereto and further stirred for 30 minutes. Next, the organic layer was taken out, and washed with a saturated saline solution.

After thus washed, it was dried with magnesium sulfate added thereto and then filtered, and the resulting filtrate was concentrated to obtain crude crystals. These were washed with water and dried at room temperature to obtain 164 g (yield: 98%) of decyl 2-phenoxycarbonylaminoacetate (Compound (1)).

The data of the compound identified by NMR analysis were:
$^1$H-NMR (CDCl$_3$, std. TMS) δ0.94 (3H), 1.25 (16H), 1.63 (2H), 4.03 (2H), 4.19 (2H), 5.58 (1H), 7.12–7.18 (5H).

Example 2

250 g of octadecyl 2-aminoacetate methanesulfonate was added to 0.5 liters of water, and stirred. An aqueous solution of 41 g of sodium acetate in 0.3 liters of water, and 78 g of phenyl chloroformate were separately put into dropping funnels, through which they were simultaneously dripped into it with taking care that the inner temperature do not exceed 50° C. These were reacted for 10 minutes, and then 41 g of sodium acetate was added thereto and further stirred for 30 minutes. The resulting suspension was filtered, and the residue was washed with acetonitrile. Dried at 40° C., 210 g (yield: 94%) of octadecyl 2-N-phenoxycarbonylaminoacetate (Compound (2)) was obtained.

The data of the compound identified by NMR analysis were:
$^1$H-NMR (CDCl$_3$, std. TMS) δ0.94 (3H), 1.25 (32H), 1.63 (2H), 4.03 (2H), 4.19 (2H), 5.58 (1H), 7.12–7.20 (5H).

Example 3

An aqueous solution of 49 g of potassium acetate in 0.3 liters of water was added to a suspension prepared by mixing 0.5 liters of ethyl acetate, 0.5 liters of water and 93 g of dodecylamine, and stirred. Through a dropping funnel, 78 g of phenyl chloroformate was dripped into it with taking care that the inner temperature do not exceed 30° C. These were reacted for 10 minutes, and then 49 g of potassium acetate was added thereto and further stirred for 30 minutes.

The resulting suspension was filtered, and the residue was washed with acetonitrile. Dried at 40° C., 75 g (yield: 49%) of N-phenoxycarbonyl-1-dodecylamine (Compound (3)) was obtained.

The data of the compound identified by NMR analysis were:
$^1$H-NMR (CDCl$_3$, std. TMS) δ0.88 (3H), 1.24 (20H), 1.59 (2H), 3.24 (2H), 5.00 (1H), 7.10–7.18 (5H).

Example 4

An aqueous solution of 41 g of sodium acetate in 0.3 liters of water was added to a suspension prepared by mixing 0.5 liters of tetrahydrofuran, 0.5 liters of water and 135 g of octadecylamine, and stirred. Through a dropping funnel, 78 g of phenyl chloroformate was dripped into it with taking care that the inner temperature do not exceed 30° C. These were reacted for 10 minutes, and then 41 g of sodium acetate was added thereto and further stirred for 30 minutes.

The resulting suspension was filtered, and the residue was washed with acetonitrile. Dried at 40° C., 183 g (yield: 94%) of N-phenoxycarbonyl-1-octadecylamine (Compound (4)) was obtained.

The data of the compound identified by NMR analysis were:
$^1$H-NMR (CDCl$_3$, std. TMS) δ0.85 (3H), 1.24 (32H), 1.58 (2H), 3.23 (2H), 4.98 (1H), 5.58 (1H), 7.14–7.18 (5H).

Example 5

68 g of phenylcarbonylmethylamine was added to 0.5 liters of ethyl acetate, and stirred. An aqueous solution of 49 g of potassium acetate in 0.3 liters of water, and 78 g of phenyl chloroformate were separately put into dropping funnels, through which they were simultaneously dripped into it with taking care that the inner temperature do not exceed 50° C. and that dripping the two is finished at the same time. These were reacted for 10 minutes, and then 49 g of potassium acetate was added thereto and further stirred for 30 minutes.

The resulting suspension was filtered, and the residue was washed with acetonitrile. Dried at 40° C., 111 g (yield: 87%) of 2-phenoxycarbonylamino-acetophenone (Compound (5)) was obtained.

The data of the compound identified by NMR analysis were:
$^1$H-NMR (CDCl$_3$, std. TMS) δ4.80 (2H), 6.10 (1H), 7.18–7.64 (8H), 8.01 (2H).

Example 6

215 g of dodecyl 3-aminopropionate was added to 0.5 liters of ethyl acetate, and stirred. An aqueous solution of 49 g of potassium acetate in 0.3 liters of water, and 78 g of phenyl chloroformate were separately put into dropping funnels, through which they were simultaneously dripped into it with taking care that the inner temperature do not exceed 50° C. and that dripping the two is finished at the same time. These were reacted for 10 minutes, and then 49 g of potassium acetate was added thereto and further stirred for 30 minutes.

The resulting suspension was filtered, and the residue was washed with acetonitrile. Dried at 40° C., 204 g (yield: 87%) of dodecyl 3-phenoxycarbonylamino-propionate (Compound (6)) was obtained.

Example 7

0.5 liters of tetrahydrofuran, 0.5 liters of water and 295 g of octadecyl 2-amino-3-phenylpropionate methanesulfonate were mixed and stirred, to which was added an aqueous solution of 49 g of potassium acetate in 0.3 liters of water. With stirring, this was well cooled with ice, into which was dripped 78 g of phenyl chloroformate through a dropping funnel with taking care that the inner temperature do not exceed 30° C. These were reacted for 10 minutes, and then 49 g of potassium acetate was added thereto and further stirred for 30 minutes.

The resulting suspension was filtered, and the residue was washed with acetonitrile. Dried at 40° C., 262 g (yield: 98%) of octadecyl 2-phenoxycarbonylamino-3-phenylpropionate (Compound (7)) was obtained.

The data of the compound identified by NMR analysis were:

$^1$H-NMR (CDCl$_3$, std. TMS) δ0.87 (3H), 1.24 (20H), 1.60 (2H), 3.20 (2H), 4.16 (2H), 4.70 (1H), 7.04–7.20 (10H).

Example 8

191 g of N-octyl-N-octadecylamine was added to 0.5 liters of ethyl acetate, and stirred. An aqueous solution of 49 g of potassium acetate in 0.3 liters of water, and 78 g of phenyl chloroformate were separately put into dropping funnels, through which they were simultaneously dripped into it with taking care that the inner temperature do not exceed 50° C. and that dripping the two is finished at the same time. These were reacted for 10 minutes, and then 49 g of sodium acetate was added thereto and further stirred for 30 minutes.

The resulting suspension was filtered, and the residue was washed with acetonitrile. Dried at 40° C., 171 g (yield: 68%) of N-phenoxycarbonyl-N-octyl-octadecylamine (Compound (8)) was obtained.

The data of the compound identified by NMR analysis were:

$^1$H-NMR (CDCl$_3$, std. TMS) δ0.89 (6H), 1.25 (43H), 1.63 (4H), 3.24 (4H), 7.08–7.20 (5H).

Production of Asymmetric Urea Compounds

In the method of asymmetric urea formation mentioned below, the reactants were stirred and reacted in a three-neck flask equipped with a mechanical stirrer and a thermometer, in an oil bath.

Example 9

423 g of octadecyl 2-aminoacetate methanesulfonate and 202 g of triethylamine were added to 1 liter of N,N-dimethylformamide, and stirred. To this was added 335 g of decyl 2-phenoxycarbonylaminoacetate, and heated up to 90° C. After reacting for 3 hours, this was cooled to 40° C., and put into 2 liters of acetonitrile. This was further cooled to room temperature, filtered. The residue was washed with acetone.

After being washed, this was dried at 40° C. for 3 days to obtain 444 g (yield: 78%) of N-(decyloxycarbonylmethyl)-N'-(octadecylcarbonylmethyl)-urea (Compound (1')).

The data of the compound identified by NMR analysis were: $^1$H-NMR (CDCl$_3$, std. TMS) δ0.86 (6H), 1.23 (48H), 1.62 (4H), 4.00 (4H), 4.15 (4H), 5.02 (2H).

The data of the elementary analysis of the compound were:

C 69.6/H 11.4/N 4.9/O 14.1 (measured),
C 69.67/H 11.34/N 4.92/O 14.06 (calculated).

Example 10

194 g of decyl 2-aminoacetate methanesulfonate and 202 g of triethylamine were added to 1 liter of N,N-dimethylformamide, and stirred. To this was added 447 g of octadecyl 2-phenoxycarbonylaminoacetate, and heated up to 90° C. After reacting for 3 hours, this was cooled to 40° C., and put into 2 liters of acetonitrile. This was further cooled to room temperature, filtered. The residue was washed with acetone.

After being washed, this was dried at 40° C. for 3 days to obtain 446 g (yield: 82%) of N-(decyloxycarbonylmethyl)-N'-(octadecylcarbonylmethyl)-urea (Compound (1')).

The data of the compound identified by NMR analysis were:

$^1$H-NMR (CDCl$_3$, std. TMS) δ0.86 (6H), 1.23 (48H), 1.62 (4H), 4.00 (4H), 4.15 (4H), 5.02 (2H).

Example 11

339 g of dodecyl 2-aminoacetate methanesulfonate and 202 g of triethylamine were added to 1 liter of N,N-dimethylacetamide, and stirred. To this was added 447 g of octadecyl 2-phenoxycarbonylaminoacetate, and heated up to 80° C. After reacting for 5 hours, this was cooled to 40° C., and put into 2 liters of acetonitrile. This was further cooled to room temperature, filtered. The residue was washed with acetone.

After being washed, this was dried at 40° C. to obtain 489 g (yield: 82%) of N-(dodecyloxycarbonylmethyl)-N'-(octadecylcarbonylmethyl)-urea (Compound (2')).

The data of the compound identified by NMR analysis were:

$^1$H-NMR (CDCl$_3$, std. TMS) δ0.86 (6H), 1.23 (52H), 1.60 (4H), 4.00 (4H), 4.15 (4H), 5.02 (2H).

Example 12

73 g of 2-methylpropylamine and 101 g of triethylamine were added to 1 liter of N,N-methylpyrrolidone, and stirred. To this was added 305 g of N-dodecyl-phenoxycarbonylamine, and heated up to 60° C. After reacting for 5 hours, this was cooled to 40° C., and put into 2 liters of methanol. This was further cooled to room temperature, filtered. The residue was washed with methanol.

After being washed, this was dried at 40° C. for 3 days to obtain 236 g (yield: 83%) of N-(2-methylpropyl)-N'-dodecyl-urea (Compound (3')).

The data of the compound identified by NMR analysis were:

$^1$H-NMR (CDCl$_3$, std. TMS) δ0.87 (9H), 1.21 (20H), 1.49 (2H), 1.75 (1H), 2.99 (2H), 3.17 (2H), 4.22 (1H), 4.30 (1H).

Example 13

185 g of dodecylamine and 101 g of triethylamine were added to 1 liter of N,N-dimethylformamide, and stirred. To this was added 305 g of N-octadecyl-phenoxycarbonyl-amine, and heated up to 90° C. After reacting for 3 hours, this was cooled to 40° C., and put into 2 liters of methanol. This was further cooled to room temperature, filtered.

The residue was suspended in acetone, and filtered. This was washed with acetone and dried 3 days to obtain 452 g (yield: 94%) of N-octadecyl-N'-dodecyl-urea (Compound (4')).

The data of the compound identified by NMR analysis were: $^1$H-NMR (CDCl$_3$, std. TMS) δ0.85 (6H), 1.22 (52H), 1.50 (4H), 3.17 (2H), 4.21 (2H).

Example 14

423 g of octadecyl 2-aminoacetate methanesulfonate and 202 g of triethylamine were added to 1 liter of N,N-dimethylformamide, and stirred. To this was added 255 g of 2-phenoxycarbonylamino-acetophenone, and heated up to 80° C. After reacting for 3 hours, this was cooled to 40° C., and put into a mixture of 1 liter of acetonitrile and 1 liter of chloroform. With stirring, this was cooled to room temperature, and filtered.

This was further washed with acetonitrile and then dried for 3 days to obtain 220 g (yield: 45%) of N-octadecyloxycarbonylmethyl)-N'-(phenylcarbonylmethyl)-urea (Compound (5')).

The data of the compound identified by NMR analysis were:

$^1$H-NMR (CDCl$_3$, std. TMS) δ0.85 (3H), 1.20 (32H), 1.61 (2H), 4.02 (2H), 4.14 (2H), 4.78 (2H), 7.35–7.64 (3H), 7.99 (2H).

Example 15

423 g of octadecyl 2-aminoacetate methanesulfonate and 537 g of octadecyl 2-phenoxycarbonylamino-3-phenylpropionate were added to 1 liter of N,N-dimethylformamide, and stirred. To this was added 202 g of triethylamine, and heated up to 90° C. After reacting for 3 hours, this was cooled to 40° C., and put into 2 liters of acetonitrile. With stirring, this was cooled to room temperature, and filtered.

This was washed with acetonitrile and then dried for 3 days to obtain 548 g (yield: 71%) of N-(dodecyloxycarbonylmethyl)-N'-dodecyloxycarbonyl-α-benzylmethyl)-urea (Compound (7')).

The data of the compound identified by NMR analysis were:

$^1$H-NMR (CDCl$_3$, std. TMS) δ0.88 (6H), 1.24 (40H), 1.61 (4H), 3.08 (2H), 3.95–4.15 (6H), 4.77 (1H), 5.00 (2H), 7.08–7.30 (5H).

Production of Barbituric Acid Derivatives

Example 16

Production of Compound B-1

20 g (37.1 mmols) of N-dodecyl-N'-octadecylurea, 4.2 g (40.8 mmols) of malonic acid, 11.3 g (111.8 mmols) of acetic anhydride and 60 ml of ethyl acetate were mixed and refluxed for 3 hours. 120 ml of methanol was added thereto, and the crystals formed were taken out through filtration to obtain 11.8 g (yield: 52%) of Compound B-1. The data to identify the Compound B-1 are as follows:

$^1$H-NMR (300 MHz, CDCl$_3$) δ0.88 (t, 6H), 1.2–1.4 (m, 48H), 1.5–1.7 (m, 4H), 3.65 (s, 2H), 3.84 (t, 4H).

Example 17

Production of Compound B-2

15 g (31.2 mmols) of N-dodecyl-N'-octadecyloxycarbonylmethylurea, 3.6 g (34.3 mmols) of malonic acid, 9.5 g (93.6 mmols) of acetic anhydride and 40 ml of ethyl acetate were mixed and refluxed for 3 hours. 50 ml of methanol was added thereto, and the crystals formed were taken out through filtration to obtain 11.8 g (yield: 69%) of Compound B-2. The data to identify the Compound B-2 are as follows:

$^1$H-NMR (300 MHz, CDCl$_3$) δ0.88 (t, 6H), 1.2–1.4 (m, 48H), 1.5–1.7 (m, 4H), 3.7 (s, 2H), 3.85 (t, 2H), 4.15 (t, 2H), 4.6 (s, 2H).

Example 18

Production of Compound B-3

28.4 g (50 mmols) of N-decyloxycarbonylmethyl-N'-octadecyloxycarbonylmethylurea, 5.7 g (55 mmols) of malonic acid, 11.2 g (110 mmols) of acetic anhydride and 50 ml of ethyl acetate were mixed and refluxed for 3 hours. 100 ml of methanol was added thereto, and the crystals formed were taken out through filtration to obtain 20 g (yield: 63%) of Compound B-3. The data to identify the Compound B-3 are as follows: $^1$H-NMR (300 MHz, CDCl$_3$) δ0.88 (t, 6H), 1.2–1.4 (m, 44H), 1.6–1.8 (m, 4H), 3.8 (s, 2H), 4.2 (t, 4H), 4.6 (s, 4H).

Fabrication and Evaluation of Diazo Thermal Recording Materials

Example 19

Preparation of Microcapsule Suspension A

To 19 parts by weight of ethyl acetate, added were 2.8 parts by weight of a diazo compound (A-1 mentioned hereinabove) and 10 parts by weight of tricresyl phosphate, and uniformly mixed. To the mixture, added was 7.6 parts by weight of a wall-forming agent, TAKENATE D-110N (by Takeda Chemical Industries), and uniformly mixed to prepare a liquid I.

The resulting liquid I was added to an aqueous phase comprising 46.1 parts by weight of aqueous 8 wt. % phthalated gelatin, 17.5 parts by weight of water and 2 parts by weight of aqueous 10% sodium dodecylbenzenesulfonate, and emulsified and dispersed at 40° C. at 10,000 rpm for 10 minutes. 20 parts by weight of water was added to the resulting emulsion, and homogenized. This was further stirred at 40° C. for 3 hours to complete encapsulation, and a microcapsule suspension A was thus obtained. In this, the particle size of the microcapsules was 0.35 µm.

Preparation of Coupler/Base Emulsion B

In 8 parts by weight of ethyl acetate, dissolved were 4 parts by weight of a coupler compound (B-3 mentioned hereinabove), 2 parts by weight of triphenylguanidine, 0.64 parts by weight of tricresyl phosphate and 0.32 parts by weight of diethyl maleate to prepare a liquid II. The liquid II was added to an aqueous phase prepared by uniformly mixing 32 parts by weight of aqueous 15 wt. % lime-processed gelatin, 5 parts by weight of aqueous 10% sodium dodecylbenzenesulfonate and 30 parts by weight of water at 40° C., and emulsified and dispersed at 40° C. at 10,000 rpm for 10 minutes. The resulting emulsion was stirred at 40° C. for 2 hours, and ethyl acetate was removed from it. The mass of ethyl acetate and water that had evaporated away was replenished with water to obtain a coupler/base emulsion B.

Preparation of Coating Liquid C 6 parts by weight of the microcapsule suspension A, 4.4 parts by weight of water, and 1.9 parts by weight of aqueous 15 wt. % lime-processed gelatin were uniformly mixed at 40° C., to which was added 8.3 parts by weight of the coupler/base emulsion B and uniformly mixed to obtain a coating liquid C for thermal recording layer.

Preparation of Coating Liquid D for protective layer 32 parts by weight of an aqueous solution of 10% polyvinyl alcohol (degree of polymerization 1700, degree of saponification 88%) and 36 parts by weight of water were uniformly mixed to prepare a coating liquid D for protective layer.

Coating

Woodfree paper was laminated with polyethylene to prepare a support for printing paper. The support was coated with the coating liquid C for thermal recording layer and the coating liquid D for protective layer in that order, and dried at 50° C. to fabricate an intended, diazo thermal recording sheet. The dry weight of the layers thus formed was 6.4 g/m$^2$ and 1.05 g/m$^2$, respectively.

Test for Color Formation and Fixation

Using a Kyocera's thermal head (KST Model), the diazo thermal recording sheet was thermally printed to form a color image thereon. The power applied to the thermal head and the pulse width were so determined that the recording energy per the unit area of the sheet could are from 0 to 40 mJ/mm$^2$. With that, the sheet was exposed overall to a 40-W UV lamp for 15 seconds of which the wavelength of the emission center is 365 nm. The density of the image area and that of the background area of the printed sheet were measured with a Macbeth densitometer.

Comparative Test for Raw-Stock Storability

One sample of the diazo thermal recording sheet was stored at room temperature, and another sample thereof was stored under a forced condition at 60° C. and 30% RH for 72 hours. The two samples were processed on a hot plate, and compared with each other in point of the difference in the color density in the image area and the difference in the fog density in the background area. To determine the density change, used was a Macbeth reflection densitometer.

Test for Lightfastness

Using a 32000-lux fluorescent lamp fastness tester, the samples that had been processed for color formation and fixation thereon in the manner as above were exposed to light continuously for 24 hours. This is to test how and to what degree the image area and the background area were faded and discolored after exposure to light. Concretely, the image area having an initial reflection density of about 1.1 was, after exposed to light, measured with a Macbeth densitometer to determine the density change in the area.

Example 20

A recording sheet was fabricated in the same manner as in Example 19, for which, however, the microcapsule suspension contained Compound (A-2) instead of Compound (A-1). Also in the same manner as in Example 19, this was processed for image formation thereon. The density of the image area and that of the background area of the printed sheet were measured with a Macbeth densitometer.

Example 21

A recording sheet was fabricated in the same manner as in Example 19, for which, however, the microcapsule suspension contained Compound (A-3) instead of Compound (A-1). Also in the same manner as in Example 1, this was processed for image formation thereon. The density of the image area and that of the background area of the printed sheet were measured with a Macbeth densitometer.

Example 22

A recording sheet was fabricated in the same manner as in Example 19, for which, however, the microcapsule suspension contained Compound (A-4) instead of Compound (A-1). Also in the same manner as in Example 19, this was processed for image formation thereon. The density of the image area and that of the background area of the printed sheet were measured with a Macbeth densitometer.

Example 23

A recording sheet was fabricated in the same manner as in Example 19, for which, however, the microcapsule suspension contained Compound (A-5) instead of Compound (A-1). Also in the same manner as in Example 19, this was processed for image formation thereon. The density of the image area and that of the background area of the printed sheet were measured with a Macbeth densitometer.

Comparative Example 1

A recording sheet was fabricated in the same manner as in Example 19, for which, however, the microcapsule suspension contained 4-N,N-dihexylamino-2-hexyloxybenzenediazonium hexafluorophosphate instead of Compound (A-1). Also in the same manner as in Example 1, this was processed for image formation thereon. The density of the image area and that of the background area of the printed sheet were measured with a Macbeth densitometer.

Comparative Example 2

A recording sheet was fabricated in the same manner as in Example 19, for which, however, the microcapsule suspension contained 4-[N-(4-methoxyphenoxyethyl)-N-hexyl]amino-2-hexyloxybenzenediazonium hexafluorophosphate instead of Compound (A-1). Also in the same manner as in Example 19, this was processed for image formation thereon. The density of the image area and that of the background area of the printed sheet were measured with a Macbeth densitometer.

Comparative Example 3

A recording sheet was fabricated in the same manner as in Example 19, for which, however, the microcapsule suspension contained 4-[N-(4-methoxyphenoxypropyl)-N-hexyl]amino-2-hexyloxybenzenediazonium hexafluorophosphate instead of Compound (A-1). Also in the same manner as in Example 19, this was processed for image formation thereon. The density of the image area and that of the background area of the printed sheet were measured with a Macbeth densitometer.

The raw-stock storability test data (color density in image area and fog density in background area before and after forced storage) of the recording sheets of Examples 19 to 23 and Comparative Examples 1 to 3 are shown below.

TABLE 1

| | | Color Density (image area) | | Fog Density (background area) | |
|---|---|---|---|---|---|
| | Color Hue λmax (nm) | before forced storage | after forced storage | before forced storage | after forced storage |
| Example 19 | 535 | 1.1 | 1.00 | 0.10 | 0.10 |
| Example 20 | 533 | 1.1 | 1.05 | 0.10 | 0.10 |
| Example 21 | 529 | 1.1 | 0.99 | 0.10 | 0.10 |
| Example 22 | 537 | 1.1 | 0.95 | 0.10 | 0.11 |
| Example 23 | 525 | 1.1 | 1.01 | 0.10 | 0.10 |

TABLE 1-continued

| | Color Hue λmax (nm) | Color Density (image area) | | Fog Density (background area) | |
|---|---|---|---|---|---|
| | | before forced storage | after forced storage | before forced storage | after forced storage |
| Comp. Example 1 | 540 | 1.1 | 0.90 | 0.21 | 0.35 |
| Comp. Example 2 | 530 | 1.1 | 0.85 | 0.17 | 0.23 |
| Comp. Example 3 | 535 | 1.1 | 0.80 | 0.22 | 0.30 |

The color image storability (lightfastness) test data (color density in image area and fog density in background area before and after exposure to light) of the recording sheets of Examples 19 to 23 and Comparative Examples 1 to 3 are shown below.

TABLE 2

| | Color Density (image area) | | Fog Density (background area) | |
|---|---|---|---|---|
| | before exposure to light | after exposure to light | before exposure to light | after exposure to light |
| Example 19 | 1.1 | 1.02 | 0.10 | 0.11 |
| Example 20 | 1.1 | 1.01 | 0.10 | 0.12 |
| Example 21 | 1.1 | 1.05 | 0.10 | 0.11 |
| Example 22 | 1.1 | 1.01 | 0.10 | 0.12 |
| Example 23 | 1.1 | 1.01 | 0.10 | 0.11 |
| Comp. Ex. 1 | 1.1 | 0.78 | 0.21 | 0.29 |
| Comp. Ex. 2 | 1.1 | 0.81 | 0.17 | 0.25 |
| Comp. Ex. 3 | 1.1 | 0.79 | 0.22 | 0.28 |

Example 24

A recording sheet was fabricated in the same manner as in Example 19, for which, however, the coupler/base emulsion contained Compound (B-1) instead of Compound (B-3). Also in the same manner as in Example 19, this was processed for image formation thereon. The density of the image area and that of the background area of the printed sheet were measured with a Macbeth densitometer.

Example 25

A recording sheet was fabricated in the same manner as in Example 19, for which, however, the coupler/base emulsion contained Compound (B-2) instead of Compound (B-3). Also in the same manner as in Example 19, this was processed for image formation thereon. The density of the image area and that of the background area of the printed sheet were measured with a Macbeth densitometer.

Example 26

A recording sheet was fabricated in the same manner as in Example 19, for which, however, the coupler/base emulsion contained Compound (B-43) instead of Compound (B-3) and additionally contained 2 parts by weight of a phenolic compound (R-1) serving as a reducing agent. Also in the same manner as in Example 19, this was processed for image formation thereon. The density of the image area and that of the background area of the printed sheet were measured with a Macbeth densitometer.

Example 27

A recording sheet was fabricated in the same manner as in Example 19, for which, however, the coupler/base emulsion contained Compound (B-44) instead of Compound (B-3). Also in the same manner as in Example 19, this was processed for image formation thereon. The density of the image area and that of the background area of the printed sheet were measured with a Macbeth densitometer.

Example 28

A recording sheet was fabricated in the same manner as in Example 19, for which, however, the coupler/base emulsion contained Compound (B-37) instead of Compound (B-3). Also in the same manner as in Example 19, this was processed for image formation thereon. The density of the image area and that of the background area of the printed sheet were measured with a Macbeth densitometer.

Comparative Example 4

A recording sheet was fabricated in the same manner as in Example 19, for which, however, the coupler/base emulsion contained 5-(2-tetradecyloxyphenyl)-cyclohexane-1,3-dione instead of Compound (B-3). Also in the same manner as in Example 19, this was processed for image formation thereon. The density of the image area and that of the background area of the printed sheet were measured with a Macbeth densitometer.

Comparative Example 5

A recording sheet was fabricated in the same manner as in Example 19, for which, however, the coupler/base emulsion contained 1-phenyl-3-octyloxycarbonylpyrazol-5-one instead of Compound (B-3). Also in the same manner as in Example 19, this was processed for image formation thereon. The density of the image area and that of the background area of the printed sheet were measured with a Macbeth densitometer.

Comparative Example 6

A recording sheet was fabricated in the same manner as in Example 19, for which, however, the coupler/base emulsion contained N-(2',5'-dibutyloxy-4'-chlorophenyl)-4,4-dimethyl-3-oxopentamide instead of Compound (B-3). Also in the same manner as in Example 19, this was processed for image formation thereon. The density of the image area and that of the background area of the printed sheet were measured with a Macbeth densitometer.

The raw-stock storability test data (color density in image area and fog density in background area before and after forced storage) of the recording sheets of Examples 24 to 28 and Comparative Examples 4 to 6 are shown below.

TABLE 3

| | Color Hue λmax (nm) | Color Density (image area) | | Fog Density (background area) | |
|---|---|---|---|---|---|
| | | before forced storage | after forced storage | before forced storage | after forced storage |
| Example 24 | 529 | 1.1 | 1.08 | 0.10 | 0.12 |
| Example 25 | 535 | 1.1 | 1.00 | 0.10 | 0.10 |
| Example 26 | 525 | 1.1 | 1.05 | 0.10 | 0.12 |
| Example 27 | 535 | 1.1 | 0.99 | 0.10 | 0.11 |
| Example 28 | 525 | 1.1 | 0.89 | 0.10 | 0.15 |
| Comp. Example 4 | 540 | 1.1 | 0.55 | 0.10 | 0.20 |
| Comp. Example 5 | 580 | 1.1 | 0.90 | 0.20 | 0.38 |
| Comp. Example 6 | 480 | 1.1 | 0.80 | 0.10 | 0.13 |

The color image storability (lightfastness) test data (color density in image area and fog density in background area before and after exposure to light) of the recording sheets of Examples 24 to 28 and Comparative Examples 4 to 6 are shown below.

TABLE 4

| | Color Density (image area) | | Fog Density (background area) | |
| --- | --- | --- | --- | --- |
| | before exposure to light | after exposure to light | before exposure to light | after exposure to light |
| Example 24 | 1.1 | 1.08 | 0.10 | 0.12 |
| Example 25 | 1.1 | 1.01 | 0.10 | 0.11 |
| Example 26 | 1.1 | 1.00 | 0.10 | 0.12 |
| Example 27 | 1.1 | 1.01 | 0.10 | 0.11 |
| Example 28 | 1.1 | 0.89 | 0.10 | 0.13 |
| Comp. Ex. 4 | 1.1 | 0.55 | 0.10 | 0.18 |
| Comp. Ex. 5 | 1.1 | 0.90 | 0.20 | 0.38 |
| Comp. Ex. 6 | 1.1 | 0.80 | 0.10 | 0.13 |

The data shown in Tables 1 to 4 confirm that the diazo thermal recording sheets containing a barbituric acid derivative of the present invention have good raw-stock storability and good image storability.

As described in detail herein above with reference to its preferred embodiments, the present invention provides novel phenylurethane compounds having a long-chain alkyl group; methods for producing the phenylurethane compounds, which start from an amino compound having a long-chain alkyl group; asymmetric urea compounds having a long-chain alkyl group; methods for producing the asymmetric urea compounds, which start from an amino compound having a long-chain alkyl group; barbituric acid derivatives useful in diazo thermal recording materials; and diazo thermal recording materials containing the barbituric acid derivative and having good raw-stock storability and good image storability.

What is claimed is:

1. A barbituric acid derivative having a molecular structure corresponding to the following general formula (20):

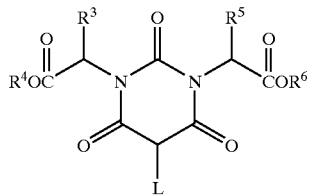

General formula (20)

wherein $R^3$ represents a hydrogen atom, an optionally-substituted alkyl group, or an optionally-substituted aralkyl group; $R^4$ represents an optionally-substituted alkyl group or an optionally-substituted aralkyl group; $R^3$ is independent of $R^4$;

wherein $R^5$ represents a hydrogen atom, an optionally-substituted alkyl group, or an optionally-substituted aralkyl group; $R^6$ represents an optionally-substituted alkyl group or an optionally-substituted aralkyl group; $R^5$ is independent of $R^6$ and L is selected from the group consisting of a hydrogen atom, a halogen atom, a dialkylaminomethyl group, phenyl-thio group and tolyl-thio group; and wherein the substituent bonded to one nitrogen atom shown in general formula (20) is different from the substituent bonded to the other nitrogen atom.

2. A barbituric acid derivative having a molecular structure corresponding to the following general formula (21):

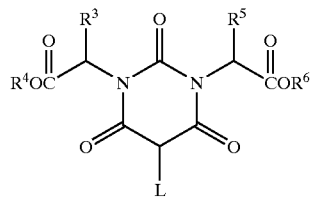

General formula (21)

wherein $R^3$ represents a hydrogen atom, an optionally-substituted alkyl group, or an optionally-substituted aralkyl group; $R^4$ represents an optionally-substituted alkyl group or an optionally-substituted aralkyl group; $R^3$ is independent of $R^4$; $R^5$ represents a hydrogen atom, an optionally-substituted alkyl group, or an optionally-substituted aralkyl group; $R^6$ represents an optionally-substituted alkyl group, or an optionally-substituted aralkyl group; $R^5$ is independent of $R^6$; and L is selected from the group consisting of a hydrogen atom, a halogen atom, alkoxy group, an aryloxy group, an acyloxy group, an alkyl or arylsulfonyloxy group, an acylamino group, an alkyl or arylsylfonamido group, an alkoxycarbonyloxy group, an aryloxycarbonyloxy group, an alkyl, aryl or heterocyclic group, a carbamoylamino group, an arylsulfinyl group, an arylsulfonyl group, a 5-membered or 6-membered nitrogen-containing heterocyclic group, an imido group, an arylazo group, an amino group, an ether group or a thioether group and wherein the substituent bonded to one nitrogen atom shown in general formula (21) is different from the substituent bonded to the other nitrogen atom.

3. A composition comprising a barbituric acid derivative according to claim 2.

* * * * *